United States Patent
Asher et al.

(10) Patent No.: US 6,214,546 B1
(45) Date of Patent: Apr. 10, 2001

(54) DETECTION OF BIOMOLECULES

(75) Inventors: Nathan Asher, Beit Shemesh; Yaron Tikochinski, Jerusalem, both of (IL); Guido Krupp, Kiel (DE); Jacob Grinberg, Tel Aviv; Adam Friedmann, Ramat Hasharon, both of (IL)

(73) Assignee: Intelligene Ltd., Jerusalem (IL)

( * ) Notice: Subject to any disclaimer, the term of this patent is extended or adjusted under 35 U.S.C. 154(b) by 0 days.

(21) Appl. No.: 08/894,727

(22) PCT Filed: Feb. 27, 1996

(86) PCT No.: PCT/US96/02380

§ 371 Date: Jul. 22, 1998

§ 102(e) Date: Jul. 22, 1998

(87) PCT Pub. No.: WO96/27026

PCT Pub. Date: Sep. 6, 1996

(30) Foreign Application Priority Data

Feb. 27, 1995 (IL) .......................................... 112799
Oct. 26, 1995 (IL) .......................................... 115722

(51) Int. Cl.$^7$ ................................ C12Q 1/68; C12P 19/34
(52) U.S. Cl. ............................................. 435/6; 435/91.31
(58) Field of Search ........................................ 435/6, 91.31

(56) References Cited

FOREIGN PATENT DOCUMENTS

| 9623569 | 8/1996 | (JP) . |
| 9413833 | 6/1994 | (WO) . |
| 9429481 | 12/1994 | (WO) . |
| 9617087 | 6/1996 | (WO) . |

OTHER PUBLICATIONS

R. Breaker et al., "A DNA enzyme that cleaves RNA", Chemistry and Biology, vol. 1, No. 4, pp. 223–229, 1941.
R. Symons, "Small Catalytic RNAs", Annual Review of Biochemistry, vol. 61, pp. 641–671, 1992.

*Primary Examiner*—John S. Brusca
(74) *Attorney, Agent, or Firm*—Browdy and Neimark

(57) ABSTRACT

The present invention concerns a method for detecting the presence of a catalytically active ribozyme in a medium. The detection of the catalytically active ribozyme may be a goal by itself, or the ribozyme may serve as a reporter for the presence of other biomolecules in an assayed sample. The detection is carried out in a catalytic system wherein the presence of the active ribozyme serves to produce other active ribozymes in a positive-feedback amplificatory manner.

29 Claims, 15 Drawing Sheets

FIG. 2a
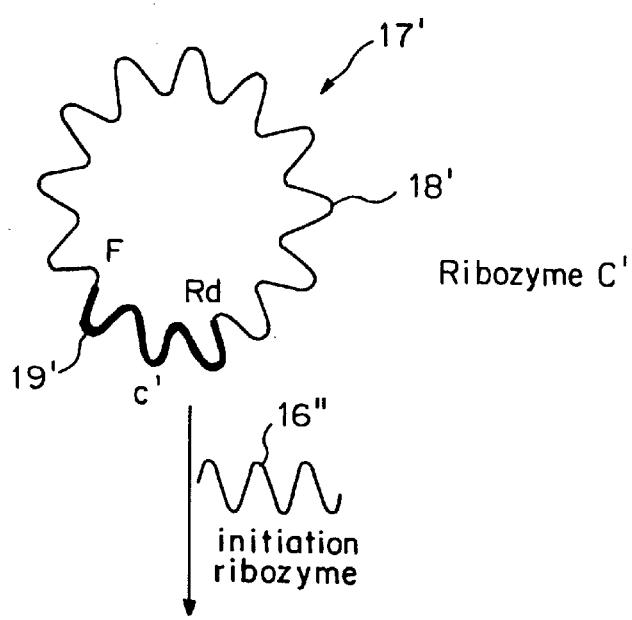
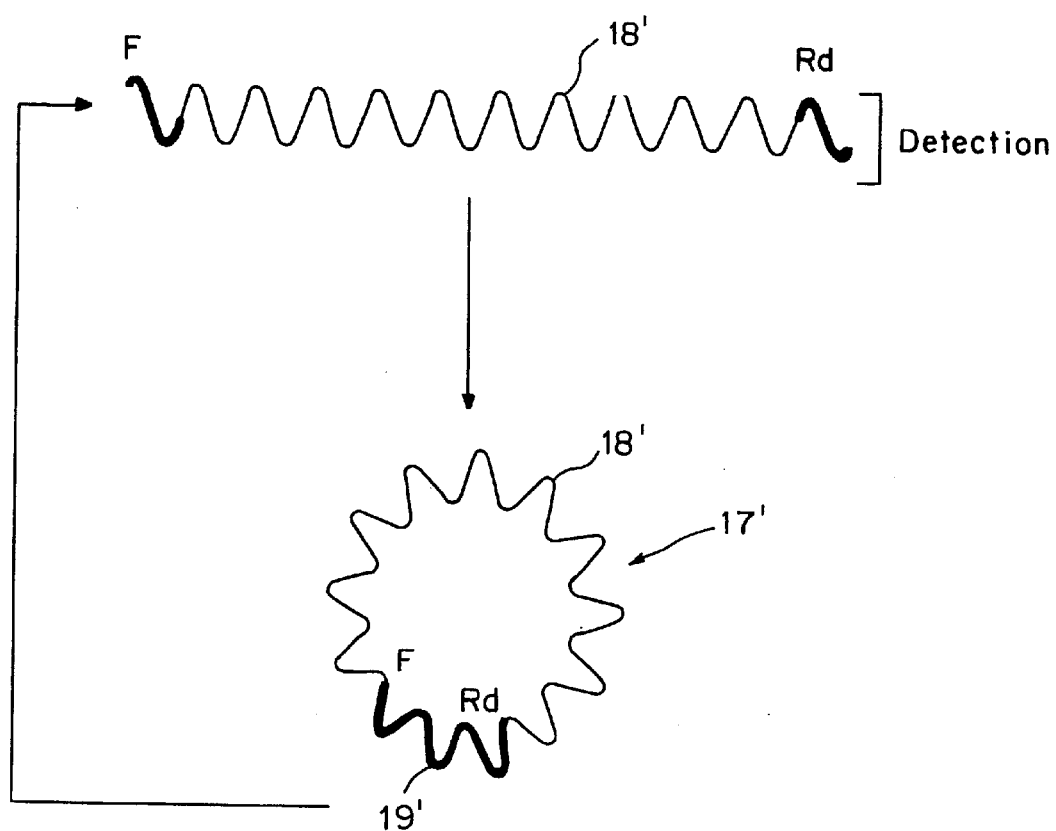

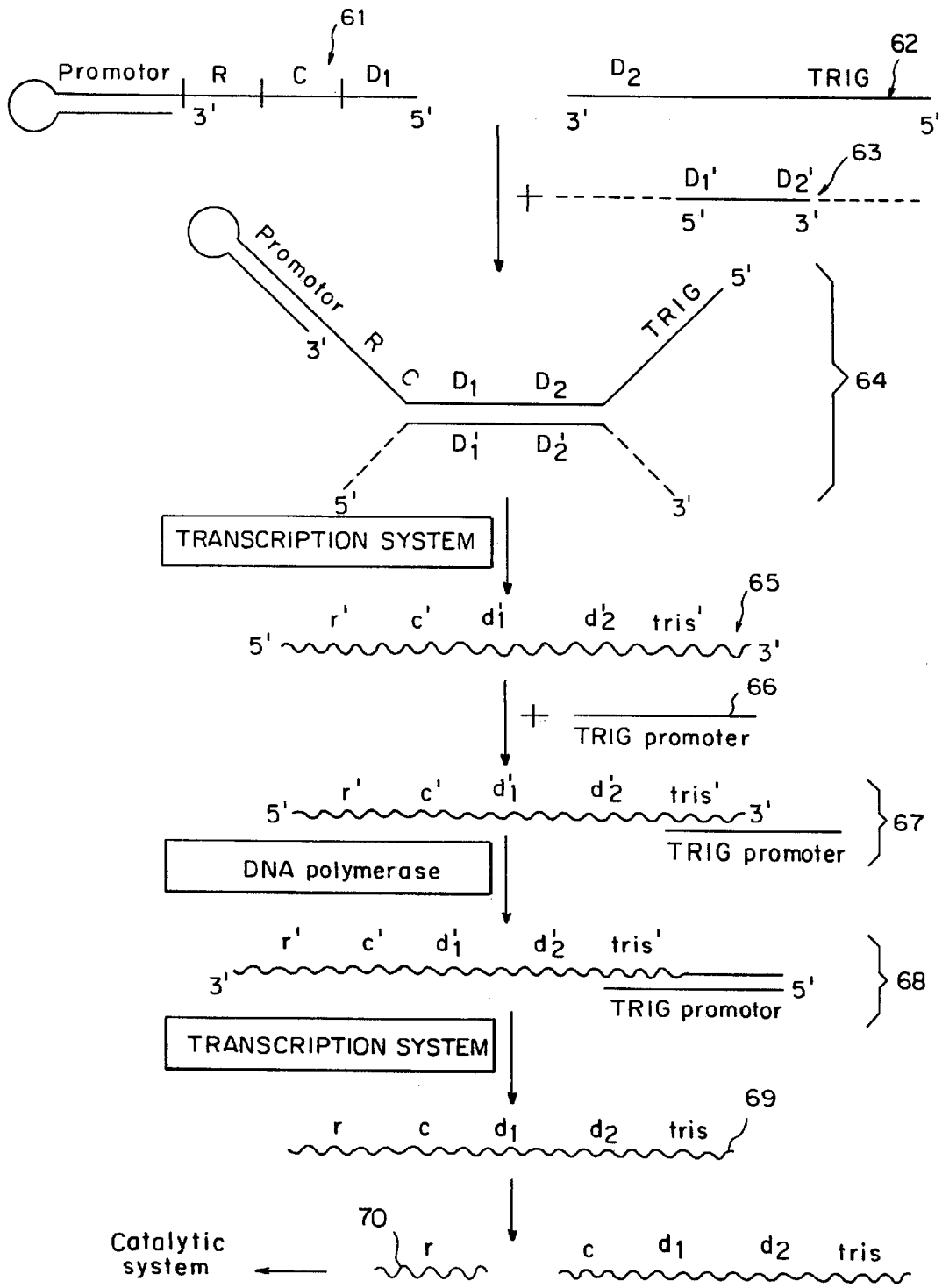
FIG. 6 DETECTION SYSTEM

FIG. 10A

| LANE | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| HH8.3-S0 | 1 | - | 1 | 1 | 1 | - | - | - | - | - | - | - | - | - | - |
| HH8.5-S0 | - | 1 | 1 | 1 | 1 | - | - | - | - | - | - | - | - | - | - |
| HH8.3-S1 | - | - | - | - | - | 1 | - | 1 | 1 | 1 | - | - | - | - | - |
| HH8.5-S1 | - | - | - | - | - | - | 1 | 1 | 1 | 1 | - | - | - | - | - |
| HH8.3-S2 | - | - | - | - | - | - | - | - | - | - | - | 1 | - | 1 | 1 | 1 |
| HH8.3-S2 | - | - | - | - | - | - | - | - | - | - | - | - | 1 | 1 | 1 | 1 |
| LAMTAR4 | - | - | 0 | 1 | 10 | - | - | 0 | 1 | 10 | - | - | 0 | 1 | 10 |
| SB824 | - | - | 5 | 5 | 5 | - | - | 5 | 5 | 5 | - | - | 5 | 5 | 5 |

FIG. 11A

| Incubation time | 1 hour | + | + | + | + | + | + | + | + |   |   |   |   |   |   |   |   |
|---|---|---|---|---|---|---|---|---|---|---|---|---|---|---|---|---|---|
|   | overnight |   |   |   |   |   |   |   |   | + | + | + | + | + | + | + | + |
| Ribozyme | SLS107 | + |   |   |   |   |   |   |   | + |   |   |   |   |   |   |   |
|   | SLS108 |   | + |   |   |   |   |   |   |   | + |   |   |   |   |   |   |
|   | SLS113 |   |   | + |   |   |   |   |   |   |   | + |   |   |   |   |   |
|   | SLS115 |   |   |   | + |   |   |   |   |   |   |   | + |   |   |   |   |
|   | SLS208 |   |   |   |   | + |   |   |   |   |   |   |   | + |   |   |   |
|   | SLS213 |   |   |   |   |   | + |   |   |   |   |   |   |   | + |   |   |
|   | SLS215 |   |   |   |   |   |   | + |   |   |   |   |   |   |   | + |   |
|   | SLS313 |   |   |   |   |   |   |   | + |   |   |   |   |   |   |   | + |

FIG. 12A

| DsLsRzA3-6 | + | + | + | + | + | + | + | + | - | - | - | - | - | - | - | - |
|---|---|---|---|---|---|---|---|---|---|---|---|---|---|---|---|---|
| HH8 | - | - | - | - | - | - | - | - | + | + | + | + | + | + | + | + |
| Blood | - | + | - | + | - | + | - | + | - | - | + | - | + | - | + | - |
| Phenol | - | - | + | + | - | - | - | - | - | - | - | + | + | - | - | - |
| Guanidine | - | - | - | - | + | + | - | - | - | - | - | - | + | + | - | - |
| SDS | - | - | - | - | - | - | + | + | - | - | - | - | - | - | + | + |

SEQUENCE LISTING

<160> NUMBER OF SEQ ID NOS: 21

<210> SEQ ID NO 1
<211> LENGTH: 38
<212> TYPE: DNA
<213> ORGANISM: Artificial Sequence
<220> FEATURE:
<223> OTHER INFORMATION: Description of Artificial Sequence: ribozyme
      linked to cleavage sequence

<400> SEQUENCE: 1
ccacugauga ggccgaaagg ccgaaacgug uccguaaa                              38

<210> SEQ ID NO 2
<211> LENGTH: 41
<212> TYPE: DNA
<213> ORGANISM: Artificial Sequence
<220> FEATURE:
<223> OTHER INFORMATION: Description of Artificial Sequence: ribozyme
      linked to cleavage sequence

<400> SEQUENCE: 2
gagacgcuga ugaggccgaa aggccgaaac acgucuggaa a                          41

<210> SEQ ID NO 3
<211> LENGTH: 68
<212> TYPE: DNA
<213> ORGANISM: Artificial Sequence
<220> FEATURE:
<223> OTHER INFORMATION: Description of Artificial Sequence: ribozyme
      linked to cleavage sequence

<400> SEQUENCE: 3
gcaacagtgg aggaaagccu acgucuggua cguccacuga ugaggccgaa aggccgaaac      60
guaguaaa                                                              68

<210> SEQ ID NO 4
<211> LENGTH: 42
<212> TYPE: DNA
<213> ORGANISM: Artificial Sequence
<220> FEATURE:
<223> OTHER INFORMATION: Description of Artificial Sequence: DNA target
      for ribozyme halves

<400> SEQUENCE: 4
gctccgagtc cacctgcacg ccgaccagtg ccgtgttcgg ga                        42

<210> SEQ ID NO 5
<211> LENGTH: 43
<212> TYPE: DNA
<213> ORGANISM: Artificial Sequence
<220> FEATURE:

```
<223> OTHER INFORMATION: Description of Artificial Sequence:  DNA target
      for ribozyme halves

<400> SEQUENCE: 5
gctccgagtc cacctgcacg ctcgaccagt gccgtgttcg gga                    43

<210> SEQ ID NO 6
<211> LENGTH: 44
<212> TYPE: DNA
<213> ORGANISM: Artificial Sequence
<220> FEATURE:
<223> OTHER INFORMATION: Description of Artificial Sequence:  DNA target
      for ribozyme halves

<400> SEQUENCE: 6
gctccgagtc cacctgcacg cttcgaccag tgccgtgttc ggga                   44

<210> SEQ ID NO 7
<211> LENGTH: 45
<212> TYPE: DNA
<213> ORGANISM: Artificial Sequence
<220> FEATURE:
<223> OTHER INFORMATION: Description of Artificial Sequence:  DNA target
      for ribozyme halves

<400> SEQUENCE: 7
gctccgagtc cacctgcacg ctatcgacca gtgccgtgtt cggga                  45

<210> SEQ ID NO 8
<211> LENGTH: 46
<212> TYPE: DNA
<213> ORGANISM: Artificial Sequence
<220> FEATURE:
<223> OTHER INFORMATION: Description of Artificial Sequence:  DNA target
      for ribozyme halves

<400> SEQUENCE: 8
gctccgagtc cacctgcacg ctatacgacc agtgccgtgt tcggga                 46

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence:  RNA
      substrate for ribozyme

<400> SEQUENCE: 9
ggucacaaug ucggucgagu ucca                                         24

<210> SEQ ID NO 10
<211> LENGTH: 35
<212> TYPE: DNA
<213> ORGANISM: Artificial Sequence
<220> FEATURE:
<223> OTHER INFORMATION: Description of Artificial Sequence: partial
      ribozyme

<400> SEQUENCE: 10
ggcgacccug augaggccgc gugcaggugg acucg                             35

<210> SEQ ID NO 11
<211> LENGTH: 32
<212> TYPE: DNA
<213> ORGANISM: Artificial Sequence
<220> FEATURE:
<223> OTHER INFORMATION: Description of Artificial Sequence: partial
``` ribozyme

<400> SEQUENCE: 11
ggaacacggc acugucggg ccgaaacauu aa                                        32

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence:  T7 RNA
      polymerase promoter oligonucleotide

<400> SEQUENCE: 12
taatacgact cactatagg                                                      19

<210> SEQ ID NO 13
<211> LENGTH: 42
<212> TYPE: DNA
<213> ORGANISM: Artificial Sequence
<220> FEATURE:
<223> OTHER INFORMATION: Description of Artificial Sequence: precursor
      ribozyme

<400> SEQUENCE: 13
ggucagcagu cgaacgcgwa auucugauga gacugcugac ca                            42

<210> SEQ ID NO 14
<211> LENGTH: 42
<212> TYPE: DNA
<213> ORGANISM: Artificial Sequence
<220> FEATURE:
<223> OTHER INFORMATION: Description of Artificial Sequence: precursor
      ribozyme

<400> SEQUENCE: 14
ggucagcagu cgaacuagwa auucugauga gacugcugac ca                            42

<210> SEQ ID NO 15
<211> LENGTH: 42
<212> TYPE: DNA
<213> ORGANISM: Artificial Sequence
<220> FEATURE:
<223> OTHER INFORMATION: Description of Artificial Sequence: precursor
      ribozyme

<400> SEQUENCE: 15
ggucagcagu cgaauauawa auucugauga gacugcugac ca                            42

<210> SEQ ID NO 16
<211> LENGTH: 42
<212> TYPE: DNA
<213> ORGANISM: Artificial Sequence
<220> FEATURE:
<223> OTHER INFORMATION: Description of Artificial Sequence: precursor
      ribozyme

<400> SEQUENCE: 16
ggucagcagu cgaaugcawa auucugauga gacugcugac ca                            42

<210> SEQ ID NO 17
<211> LENGTH: 42
<212> TYPE: DNA
<213> ORGANISM: Artificial Sequence
<220> FEATURE:
<223> OTHER INFORMATION: Description of Artificial Sequence: precursor
      ribozyme

```
<400> SEQUENCE: 17
ggucagcagu cgaacuagwa cgucugauga gacugcugac ca                  42

<210> SEQ ID NO 18
<211> LENGTH: 42
<212> TYPE: DNA
<213> ORGANISM: Artificial Sequence
<220> FEATURE:
<223> OTHER INFORMATION: Description of Artificial Sequence: precursor
      ribozyme

<400> SEQUENCE: 18
ggucagcagu cgaauauaua cgucugauga gacugcugac ca                  42

<210> SEQ ID NO 19
<211> LENGTH: 42
<212> TYPE: DNA
<213> ORGANISM: Artificial Sequence
<220> FEATURE:
<223> OTHER INFORMATION: Description of Artificial Sequence: precursor
      ribozyme

<400> SEQUENCE: 19
ggucagcagu cgaaugcawa cgucugauga gacugcugac ca                  42

<210> SEQ ID NO 20
<211> LENGTH: 42
<212> TYPE: DNA
<213> ORGANISM: Artificial Sequence
<220> FEATURE:
<223> OTHER INFORMATION: Description of Artificial Sequence: precursor
      ribozyme

<400> SEQUENCE: 20
ggucagcagu cgaauauawa gcucugauga gacugcugac ca                  42

<210> SEQ ID NO 21
<211> LENGTH: 36
<212> TYPE: DNA
<213> ORGANISM: Artificial Sequence
<220> FEATURE:
<223> OTHER INFORMATION: Description of Artificial Sequence: ribozyme

<400> SEQUENCE: 21
ggcgacccug augaggccga aaggccgaaa cauuaa                         36
```

DETECTION OF BIOMOLECULES

FIELD OF THE INVENTION

The present invention concerns a method and kit for the detection of the presence of catalytically active ribozymes in a medium. The method and kit of the invention may be useful within the framework of a method and kit for the detection of the presence of specific biomolecules in a test sample.

BACKGROUND OF THE INVENTION

Detection of the presence of specific biomolecules, such as DNA or RNA sequences, proteins, antigens, antibodies, etc., in a sample is required for a variety of experimental, diagnostic and therapeutic purposes. A multitude of assays are available for detecting proteinaceous biomolecules such as gel electrophoretogram, HPLC, affinity chromatography, as well as other assays which are performed by use of an appropriately labelled probe. While such assays are satisfactory where the proteinaceous biomolecule to be detected is present in sufficiently large quantities, they are at times not sensitive enough to allow detection of minute quantities of biomolecules.

DNA or RNA sequences can be detected by the use of a labelled probe. Where the DNA or RNA sequences to be detected present in only very small amounts, they have to be amplified by methods such as LCR (ligase chain reaction), SSR (self-sustained sequence replication) or PCR (polymerase chain-reaction).

Although amplification methods such as PCR have had an extremely high impact on basic research, they have been slow in making the transition to the clinical setting. The primary reason for this is that the requirement for automation combined with the clinical environment of the samples, have yielded processes that are complex, slow and expensive. The need for protein enzymes with their high sensitivity to environmental factors necessitates a very controlled environment in which they are to operate. Typically, a clinical sample contains many components that can interfere with the enzyme's ability to perform its catalytic activity. In addition, the standard methods that are used for sample preparation to release the nucleic acids, such as Guanidine thiocyanate or Phenol extraction are unsuitable for protein based enzymatic activity and it is therefore necessary to remove the target nucleic acid from sample preparation.

Ribozymes are typically RNA molecules having enzyme-like catalytic activities that are usually of cleavage, splicing or ligation of nucleic acid sequences. The known substrates for ribozymes are RNA molecules although there have been some indications that ribozymes may act on DNA molecules and on proteins.

Natural ribozymes which participate in intracellular reaction work in cis, catalyzing only a single turnover, and are usually self-modified during the reaction. However, ribozymes can be engineered to act in trans, in a truly catalytic manner, with a turnover greater than one and without being self-modified. Two distinct regions can be identified in a ribozyme: the binding region which gives the ribozyme its specificity through hybridization to a specific nucleic acid sequence (and possibly also to specific proteins), and a catalytic region which gives the ribozyme the activity of cleavage, ligation or splicing. Each class of ribozymes cleaves a different sequence of nucleotides using a distinct mechanism of action. Each class is further distinguished by the number of nucleotide bases that are essential for its catalytic activity and by the degree of the specificity of the ribozyme and the target sequence (Robert H. Simons, *Annual Review of Biochemistry*, 61, pp. 641–671, (1992)).

It has recently been proposed to use ribozymes in order to treat diseases or genetic disorders by cleaving a target RNA, such as viral RNA or messenger RNA transcribed from genes that should be turned off. This method is proposed as an alternative to blockage of the RNA transcript by the use of antisense sequences. Owing to the catalytic nature of the ribozyme, a single ribozyme molecule cleaves many molecules of target RNA and therefore therapeutical activity is achieved in relatively lower concentrations than those required in an antisense treatment (WO 96/23569).

The use of ribozymes for diagnostic purposes has been only seldomly mentioned. WO 94/13833 describes a method for detecting nucleic acid molecules in a solution by tailoring a specific ribozyme molecule having two regions, one complementary to the nucleic acid sequence to be detected, and the other complementary to a co-target molecule bearing a detectable label. The ribozyme is able to specifically and reversibly bind both a selected target nucleic acid sequence and to the labelled co-target. When both the target and the co-target are bound, the ribozyme undergoes a conformational change which renders it active and able to cleave the label off the co-target, and the free label can then be detected. Upon cleavage of the co-target, the ribozyme is able to re-associate with an additional co-target, cleaving more label and producing more detectable signals.

Although the inventors of WO 94/13833 termed their invention "amplification of signal" there is actually no amplification in the number of ribozymes produced, but rather the reaction is purely an enzymatic reaction, wherein the catalytic substance (in this case the ribozyme) cleaves the substrate (in this case the co-target) and then disassociate and cleave another substrate. There is no true amplification of the number of active ribozymes involved in the reaction occurs.

GLOSSARY

Below is a glossary of terms which are used in the following description and claims. However, this glossary should not be considered separately and for full comprehension of the various terms and the meaning in which these terms have in the context of the invention, the glossary should be read in conjunction with the remainder of the disclosure herein.

Ribozyme—a nucleic acid molecule which possesses an enzyme-like catalytic activity. The term "ribozyme" as used in the art generally refers to RNA molecules having a catalytic activity although in the context of the present invention this term is used to denote a catalytically active (enzyme-like) oligonucleotide in general. The ribozyme of the invention may thus be an RNA molecule, may be an oligonucleotide comprising dNTPs or composed completely of dNTPs and may also comprise a variety of non-naturally occurring nucleotides such as IsoG or IsoC 5'-O-(1-thiotriphosphate) nucleosites and 5-O-methyl nucleotides. The ribozyme which may be used in accordance with the present invention may be comprised exclusively of nucleic acids as described above or may require a co-factor for their catalytic activity. The ribozymes may have a catalytic activity of cleavage, ligation, splicing or splicing-out (removal) of oligonucleotide sequence, addition of groups to oligonucleotides, rearrangement of nucleic acid sequences, etc.

Assayed biomolecule—a molecule the presence of which in the test sample is to be detected. It can be an oligonucleotide or a member of a recognition pair such as receptor/ligand, antibody/antigen, lectin/glycoprotein, etc.

Initiation ribozyme—The ribozyme which initiates the reaction where more ribozymes are produced, eventually leading to the generation of a detectable label. Where the method of the invention is used to detect biomolecules, the initiation ribozyme is part of the detection system (see below), and serves as a reporter for the presence of the assayed biomolecule, since only in the presence of said assayed biomolecules it is either generated or it becomes catalytically active. The presence of an active initiation ribozyme activates the catalytic system (see below).

Detection system—the combination of molecules and reagents that enable the production or activation of a catalytically active initiation ribozyme, which serves as a reporter for the presence of the assayed biomolecules in the test sample. In other words, in the presence of the assayed biomolecules, following a reaction or a cascade of reactions, a catalytically active initiation ribozyme is eventually generated. The presence of the initiation ribozyme is verified in the catalytic system (see below) where it brings to the generation of more active ribozymes in an amplificatory manner (the ribozymes themselves or a product of their catalytic activity, e.g. a free label is then detected at the final stage of the assay).

Inactive ribozyme—a potentially catalytically active ribozyme which cannot exert its catalytic activity (cleavage, splicing, ligation, etc.) until it has been modified, or until the conditions in the medium have not been amended to such in which it becomes active.

Activation—rendering an inactive ribozyme catalytically active by some kind of catalytic action (cleavage, splicing, ligation, addition of groups, rearrangement), or by change of external conditions (such as addition of magnesium ions).

Inhibitory moiety—a moiety which may at times be present in the second complex molecule (see below) and which when present renders the initiation ribozyme inactive. The inhibitory effect of the inhibitory moiety can be terminated by its modification or removal from the complex molecule.

Complex molecule—a molecule which forms part of the detection system in accordance with an embodiment of the invention referred to herein as the "activation embodiment". In one mode of carrying out the activation embodiment, a "first complex molecule" is being used, which comprises an initiation ribozyme which is a priori, catalytically inactive (for example, due to lack of magnesium ions in the medium) linked to a sequence capable of being cleaved by an active initiation ribozyme and comprising in addition a recognition biomolecule (see below). In another mode of carrying out the activation embodiment, a "second complex molecule" is being used, which comprises an initiation ribozyme which is a priori, catalytically inactive and is linked to a sequence capable of being cleaved by an active initiation ribozyme and comprising in addition a recognition biomolecule (see below). The second complex molecule further comprises an inhibitory moiety.

Recognition biomolecule—a molecule capable of specifically recognizing and binding to the assayed biomolecule. Where the assayed biomolecule is an oligonucleotide sequence, the recognition biomolecule is the complementary sequence. Where the assayed biomolecule is a member of a recognition pair (such as antigen-antibody) the recognition biomolecule is the other member of the pair.

First oligonucleotide—an oligonucleotide, typically a DNA molecule, which comprises from 3'→5': a double-stranded functional promotor, a single-stranded sequence that codes for a sequence complementary to the sequence of the initiation ribozymes, a single-stranded sequence identical (with the necessary U→T replacements) with an RNA sequence capable of being cleaved by a catalytically active initiation ribozyme, and a single-stranded sequence complementary to the 5'-part of the oligonucleotide sequence to be detected.

Second oligonucleotide—an oligonucleotide, typically a DNA molecule, which comprises from 3'→5': a single-stranded 3'-part complementary to the oligonucleotide sequence to be detected, and a triggering oligonucleotide template (see below).

Triggering oligonucleotide template—an oligonucleotide sequence which is part of the second oligonucleotide, the transcription product of which is capable of hybridizing with the back promotor construct (see below).

Triggering oligonucleotide sequence—the transcriptional product of the triggering oligonucleotide template, capable of hybridizing with the back promotor construct (see below) and after the back promotor has been completed, can bring to transcription of an oligonucleotide sequence to which it is attached.

Non-template strand oligonucleotide—the transcription product of the oligonucleotide hybrid obtained by hybridization of the assayed nucleic acid sequence, the first oligonucleotide and the second oligonucleotide, and which comprises from 3'→5': a triggering oligonucleotide sequence, a sequence complementary to the assayed biomolecule, a sequence complementary to a sequence which can be cleaved by the initiation ribozyme, and a sequence complementary to the initiation ribozyme.

Back promotor construct—a single-stranded promotor sequence attached to a single-stranded sequence capable of hybridizing with the triggering oligonucleotide sequence. After hybridization with the triggering oligonucleotide sequence, and upon action of a suitable DNA polymerase, a functional double-stranded promotor is created, which in the presence of a transcription system (see below) is capable of producing the final oligonucleotide transcript (sec below).

Final oligonucleotide transcript—the transcriptional product of the oligonucleotide hybrids obtained following hybridization of the back promotor construct, non-template strand oligonucleotide (after the promotor has been completed by a suitable DNA polymerase to a double-stranded functional promoter), and comprises from 5'→3': an initiation ribozyme sequence, a sequence capable of being cleaved by said initiation ribozyme, a sequence that codes for the complement of the detected sequence on the assayed biomolecule, and a sequence that codes for the complement of the triggering oligonucleotide template. The initiation ribozyme in said final oligonucleotide transcript can cleave its adjacent sequence thus freeing itself and yielding a free, fully active initiation ribozyme.

Third oligonucleotide sequence—a nucleic acid sequence complementary to the 5'-part of the sequence to be detected in the assayed biomolecule.

Third composite molecule—a molecule used in the "assembly embodiment" of the invention, and which comprises the third oligonucleotide sequence linked to part of the initiation ribozyme. It optionally also comprises a sequence cleavable by an active initiation ribozyme.

Fourth oligonucleotide sequence—an oligonucleotide sequence complementary to the 3'-part of the sequence to be detected in the assayed biomolecule.

Fourth composite molecule—a molecule used in the "assembly embodiment" of the invention which comprises the fourth oligonucleotide sequence linked to part of the initiation ribozyme required to complete the part present in the third composite to obtain a complete catalytically active ribozyme. It optionally also comprises a sequence cleavable by an active initiation ribozyme.

Catalytic system—An ensemble of molecules and reaction mixtures which in the presence of a catalytically active initiation ribozyme produces a detectable signal. This ensemble of molecules comprises a combination of composite molecules comprising a ribozyme which is a priori inactive. By one embodiment, the catalytic system comprises reagents and a combination of a first composite molecule and a second composite molecule (see below), comprising a first and second ribozyme (inactive), respectively. The first and second ribozymes are a priori inactive and either or both can be activated by a catalytically active initiation ribozyme. Active first ribozyme may activate inactive second ribozyme molecules, and active second ribozymes may activate inactive first ribozyme to cause amplification of the number of active ribozymes in a positive feedback manner. Alternatively, the first and second ribozymes may be immobilized or spatially separated from each other and cleavage of one or both by the initiation ribozyme causes their release to the medium. Released, free ribozymes can free immobilized second ribozymes (for example by cleavage) and free second ribozymes can in turn release and free first ribozyme, thus giving rise to self amplifying reaction cascade which rapidly yields an amplification in the number of active ribozymes in a positive feedback manner.

The catalytic system may also comprise in accordance with another embodiment, only one species of composite molecules which are immobilized or spatially separated from each other in the reaction vessel or which are a priori inactive. An initiation ribozyme activates the inactive ribozyme or releases the ribozyme from the composite molecule and active or released ribozymes then act to respectively activate inactive or free immobilized other ribozymes, then giving rise to a self amplifying reaction cascade which rapidly yields an amplfication in the number of active ribozymes in a positive feedback manner.

As a result of ribozyme activation or release, a detectable signal is produced which signal is indicative to the presence of the initiation ribozyme in the medium.

First composite molecule—comprises a first ribozyme (see below), optionally labelled, linked to second nucleic acid sequence (see below).

Second composite molecule—comprises a seconded ribozyme (see below), optionally labelled, linked to a first nucleic acid sequence (see below).

First nucleic acid sequence—an oligonucleotide sequence which is part of the second composite molecule and which is a target for the catalytic activity of the first ribozyme (see below). Following the catalytic activity of the first ribozyme on the first nucleic acid sequence, the second ribozyme (see below) is either released into the medium or becomes catalytically active.

Second nucleic acid sequence—an oligonucleotide sequence which is part of the first composite molecule and which is a target for the catalytic activity of the second ribozyme (see below). Following the catalytic activity of the second ribozyme on the second nucleic acid sequence, the first ribozyme (see below) is either released into the medium or becomes catalytically active.

First ribozyme—part of the first composite molecule—is capable of cleaving the first nucleic acid sequence and is identical in its catalytic activity to the initiation ribozyme. It is optionally labelled.

Second ribozyme—part of the second composite molecule—is capable of cleaving the second nucleic acid sequence and is optionally labelled.

Third ribozyme—a ribozyme which may form part of the catalytic system in accordance with another embodiment thereof. The third ribozymes are initially inactive. Initiation ribozyme acts to activate the third ribozyme by exerting its catalytic activity thereon (in a manner to be explained below) and the activated ribozymes can then act, to activate other third ribozymes in the catalytic system.

Transcription system—ensemble of oligonucleotide, nucleotides, RNA polymerase and reagents which, in the presence of an oligonucleotide template bring to the transcription of an oligonucleotide transcript.

Fourth ribozyme—a ribozyme which is part of the catalytic system in accordance with an embodiment thereof, and which once catalytically active can ligate two parts of the fifth ribozyme (see below) to produce a catalytically active fifth ribozyme. The fourth ribozyme is composed of at least two components, which are initially separated, and which are ligated together by the fifth ribozyme (when catalytically active). Following such ligation, the fourth ribozyme becomes catalytically active.

Fifth ribozyme—a ribozyme which is part of the catalytic system comprising the fourth ribozyme and which once catalytically active can ligate together two parts of the fourth ribozyme to produce a catalytically active fourth ribozyme. The fifth ribozyme is composed of at least two components, which are initially separated and which are ligated together by the fourth ribozyme. Following such ligation, the fifth ribozyme becomes catalytically active.

Sixth ribozyme—a specific example of the third ribozyme wherein the inactive ribozyme carries an extra nucleic acid sequence, and is activated upon cleavage or splicing-out (i.e. removal) of this sequence.

Seventh ribozyme—a ribozyme wherein the assayed nucleic acid sequence completes a missing portion essential for its catalytic activity, and thus once combined with the assayed sequence it becomes catalytically active.

SUMMARY OF THE INVENTION

The present invention provides a ribozyme-based signal-amplification method which is relatively simple to perform, is rapid and inexpensive. Unlike hitherto available detection-amplification methods, the method of the invention is also suitable for a point-of-care (POC) testing.

One advantage of the method of the invention is in that ribozymes are active under conditions found in the clinical environment, e.g. in bioligical fluids. Furthermore, as will be shown further below, the signal-amplification method in accordance with the invention does not require the observance of specific conditions in order to ensure specificity (strict observance of conditions is a must in prior art signal-amplification methods). Additionally, ribozymes are functional in various sample preparation cocktails, e.g. 1 M Guanadine thiocyanate as well as in a saturated phenol preparation, which usually inhibits function of other detection-amplification systems.

Ribozymes are composed of nucleic acid sequences and thus assay and probe sequences can be included in the ribozyme molecule. Furthermore, it is possible to increase the specificity of the amplification process by engineering the ribozyme such that part of the assayed sequence itself is required for the ribozyme to exert its catalytic activity.

A very powerful technique, termed in the art as "in vitro evolution" has been successfully applied to ribozymes to produce a ribozyme with various catalytic activities and specificities. By such techniques, a vast array of potential ribozymes are screened for activity. Those ribozymes that show activity are purified for further rounds of selection and after repeated rounds only the most potent candidates remain. In traditional amplification techniques, following a choice of the enzyme, the environment where the enzyme is to operate, i.e. the sample-comprising medium, has to be modified to allow proper activity of the enzyme. In the case of ribozymes, using in vitro evolution, it is possible to select a ribozyme which is highly active in a desired clinical (biological) medium, by performing the in vitro evolution in a selection medium which is identical in its composition to the clinical sample.

The present invention provides a sensitive method for the detection of a catalytically active ribozyme (referred to herein as "initiation ribozyme") in a medium. Detection of the presence of a catalytically active initiation ribozyme may be a goal by itself, although usually the catalytically active initiation ribozyme serves as reporter for the presence of other biomolecules in the test sample. Once a medium comprising an active initiation ribozyme is introduced into a catalytic system in accordance with the invention, there results a catalytic reaction cascade which gives rise to an exponential amplification in the number of active ribozymes. The catalytic system comprises ribozymes which are either inactive or spatially separated from one another such that they cannot exert their catalytic activity; the initiation ribozyme frees or activates ribozymes of the catalytic system which in turn free or activate respectively, further ribozymes of the system. The ribozymes either carry a detectable label or the catalytic activity causes generation of a detectable label, which then serves as an indication of the catalytic cascade which occurred in the system.

According to embodiments of the present invention in which the ribozymes are initially immobilized, the presence of free ribozymes in the reaction medium may serve as a detectable signal by itself. In accordance with another embodiment, each active ribozyme is made to carry or produce a detectable label and these then serve as the detectable signal.

According to the method of the invention there is very little false positive signal, i.e. low noise level; furthermore the method of the invention enables the detection of several biomolecules in a single assay system.

The present invention thus provides a method for detecting the presence of a catalytically active initiation ribozyme in a medium, comprising the steps of:

(a) providing a catalytic system comprising
  (aa) ribozymes which are a priori catalytically inactive or spatially confined such that they cannot exert their catalytic activity on their target; the target of the ribozymes being other ribozymes of the catalytic system, their catalytic activity on such other ribozymes causing either:
    (i) activation of inactive ribozymes,
    (ii) release of spatially confined ribozymes to allow them to reach their targets;
at least some of the ribozymes of the catalytic system being a target of the catalytic activity of the initiation ribozyme, the catalytic activity of the initiation ribozyme on said some of the ribozymes being that of (i) or (ii) above; and comprising
  (ab) a detectable label having detectable properties such that the catalytic activity of the ribozymes causes a change in the detectable properties;

(b) contacting the medium with said catalytic system;
(c) providing conditions permitting said catalytically active initiation ribozyme and catalytically active ribozymes of the catalytic system to exert their catalytic activity, whereby the presence of a catalytically active initiation ribozyme gives rise to a reaction cascade in which ribozymes of the catalytic system are activated or freed into the medium; and
(d) detecting said detectable properties, a change in said properties being an indication of the presence of an active initiation ribozyme in said medium.

The prime utility of the ribozyme detection method of the invention, is within the framework of an assay designed to detect the presence of a biomolecule such as: a specific nucleic acid sequence, a member of a binding couple such as antibody-antigen, sugar-lectin, etc., in a biological sample. Such an assay may conceptually be thought of as comprising two distinct components (although these components may be included physically together in a single reaction vessel): a detection system and a catalytic system. In such an assay, the presence of the assayed biomolecule brings to the production, in a manner to be described further below, of a catalytically active initiation ribozyme in the medium. The catalytically active initiation ribozyme then acts as a reporter molecule in the catalytic system, giving rise, following a reaction cascade which amplifies the number of active ribozymes, to the appearance of a detectable label in the reaction medium as generally described above. The appearance of such a detectable label in the medium of the catalytic system thus indicates the presence of the assayed biomolecule in the original assayed biological sample.

DETAILED DESCRIPTION OF THE INVENTION

In accordance with the invention, novel use is made of ribozymes. In the most generalized sense, a catalytic system comprising ribozymes is used for the detection of the presence of a catalytically active initiation ribozyme in an assayed medium. Detection of the presence of a catalytically active initiation ribozyme in an assayed medium may be a goal by itself, for example, in the process of preparation of ribozymes by in vitro evolution. In addition, in accordance with a preferred embodiment of the invention, the catalytically active initiation ribozyme serves as a reporter for the presence of an assayed biomolecule (other than the initiation ribozyme) in an assayed biological sample.

The ribozymes used in accordance with the invention may be comprised entirely of RNA. At time it is possible also to replace some of the ribonucleotides ("rNTPs") in the RNA with deoxy nucleotides ("dNTPs") or some other naturally or non-naturally occurring nucleotides such as IsoG or IsoC 5'-O-(1-thiotriphosphate) nucleotsites and 5-O-methyl nucleotides. Such replacement is at times desired, for example, to increase stability of the ribozyme to RNAase which are present in almost all biological samples. While this will not specifically be mentioned at each time, it is understood that the term "ribozyme" means to denote catalytic nucleotides composed entirely of rNTPs or catalytic oligonucleotides wherein some of the rNTPs have been replaced by dNTPs or other nucleotides. The ribozyme may also be entirely composed of DNA (Breaker et al., *Chemistry and Biology,* 1(4):223–9, 1994).

The ribozymes of the invention may comprise of nucleic acid sequences as described above complexed with a non-nucleic acid molecule such as a protein, polypeptide, fatty-acid, dye, antibiotic, or a carbohydrate. The non-nucleic acid moiety complexed with the ribozyme may serve as a co-factor for the ribozyme's catalytic activity.

In the following, use of the term "oligonucleotide" will be made.

The oligonucleotides may, depending on the context, be a DNA oligonucleotide (consisting entirely of dNTPs) or a RNA oligonucleotide (consisting entirely of rNTPs). However, specifically in the case of RNA oligonucleotides, it is at times desired to replace some or all of the rNTPs with dNTPs or other naturally and non-naturally occurring nucleotides.

The present invention provides, in its broadest sense, a method for the detection of the presence in a tested medium of a catalytically active initiation ribozyme. By "catalytically active", it is meant that a ribozyme is capable of carrying out a catalytic reaction such as cleavage, splicing, ligation, addition of specific groups such as phosphate to molecules, rearrangement of nucleic acid sequences and the like.

The catalytic system in accordance with one embodiment for carrying out the invention comprises two species of ribozymes which are a priori inactive, but become catalytically active as a result of the exertion of a catalytic activity thereon. For example, each ribozyme may have a nick or break in a portion essential for its activity and prior ligation of this nick or break is thus required for its activation. The catalytic system in this case comprises two species of ribozymes, each species a priori broken into two components and thus initially inactive. An active ribozyme of one species is capable of ligating the two components of the second species of ribozyme thus rendering it active, and an active ribozyme of the second species of ribozyme is capable of ligating the two components of the first species of ribozymes, thereby rendering it active. Then the activation proceeds by cross-ligation in a positive feedback amplificatory manner.

The first active ribozyme of one species may be produced by the initiation ribozyme which is a product of the detection system, in one of two routes. According to one route, some of the ribozymes of the first species are a priori fully assembled but cannot ligate the parts of the second species of ribozyme, since they are spatially separated therefrom, for example, as a result of being immobilized by means of a porous membrane, etc. The initiation ribozyme cleaves the molecules of the immobilized fully assembled first species of ribozyme, and the free first species of ribozyme then ligates the second species of ribozymes which can in turn ligate members of the first species of the ribozyme which are not, a priori, assembled and so on.

According to the second route, the initiation ribozyme is itself a ligating ribozyme which ligates from its parts, at least one species of the two ribozyme of the catalytic system, thus initiating the cross-ligation cascade. In such a case there is no need to spatially separate various members of the catalytic system since until the initiation ribozyme is introduced to the reaction mixture no catalytic process can begin.

Another example are ribozymes which have a redundant sequence which renders the ribozyme inactive and it thus needs to be either cleaved or spliced-out for the ribozyme's activation. Further example are ribozymes which require sequence rearrangement or addition of specific groups for activation. Yet another example are ribozymes which require reverse exon splicing, i.e. addition of a sequence internal to the ribozyme.

One species of ribozymes when in the active form, may activate inactive ribozymes of the second species and vice versa, as it possesses the catalytic properties (ligation, cleavage, splicing, rearrangement, etc.) required to modify the other species of ribozyme from an inactive to an active form. The two ribozymes may potentially possess the same type of catalytic activity (e.g. both are ligating rizoymes or both cleaving ribozymes, etc.) or may possess different types of catalytic activities.

One or both species of the a priori inactive ribozymes is activated by a catalytically active initiation ribozyme. Prior to introduction of the initiation ribozyme to the medium, the catalytic system is essentially silent as no catalytic activity takes place. In the presence of such an initiation ribozyme, a ribozyme amplification cascade begins since each active ribozyme generates in turn more active ribozymes in a positive feedback manner. Active ribozymes give rise to a signal which can be detected in a manner as described hereinbelow and such a signal is indicative to the presence of the original catalytically active initiation ribozyme in the medium.

The catalytic system in accordance with another embodiment for carrying out the invention comprises two species of composite molecules, each comprising a ribozyme linked to a cleavable nucleic acid sequence. The ribozyme in one species of composite molecules is capable of cleaving the nucleic acid sequence in the other species of composite molecules so that cross-cleavage between the two species of composite molecules is, in principle, possible, while self-cleavage is avoided. However, prior to introduction of the initiation ribozyme to the medium, cross-cleavage does not result since the two species of composite molecules are constructed so as to prevent mutual interaction between them, while cleaved ribozymes are able to interact with other composite molecules in the test vessel and further release ribozymes to the medium in a positive feedback manner.

Prevention of mutual interaction can be done, for example, by immobilizing each species of composite molecules to opposite sides of the test vessels; by linking each species of the composite molecule to different beads or different colloid particles having properties, e.g. size or other properties, e.g. the same electric charge (which repels the beads from one another) which prevents any kind of interaction between molecules attached to one with molecules attached to another; by linking the composite molecules to moieties having the same electric charge, so that the electrical rejection between said moieties will prevent any interaction between the two composite molecules; by placing each species of composite molecules at opposite sides of a porous membrane which does not allow permeation therethrough of the full composite molecule, but allows free passage of cleaved ribozyme.

A catalytically active initiation ribozyme, either present in the test medium a priori, or produced as a result of the presence of another biomolecule in a biological sample (such a ribozyme being in this case) ("a reporter ribozyme") is able to cleave a specific nucleic acid present in one or both species of composite molecules thus freeing the ribozymes of the catalytic system. The cleaved ribozymes are able to interact freely in the reaction vessel with the ribozymes from the other species of composite molecules, which in turn, can again cleave the ribozymes from the first species of composite molecules, thus creating a "ping-pong" cross-cleavage of ribozymes. Such cross-cleavage of ribozymes acts in a positive feedback manner, causing substantial amplification of the reaction. Either or both species of ribozymes typically bears detectable labels. The detection of cleaved labels, indicates the presence of the catalytically active initiation ribozyme in the reaction mixture. Where the initiation ribozyme is a reporter ribozyme, detection of a free label indicates the presence of an assayed biomolecule in the reaction mixture.

The catalytic system may comprise, in accordance with other embodiment, only one species of inactive ribozymes or one species of composite molecules comprising a ribozyme and a nucleic acid sequence cleaved by the ribozyme when converted into a free or active form. In an analogous manner to that described above for the said one embodiment, each single molecule of the ribozyme is inactive until the catalytically active initiation ribozyme is introduced to the medium: for example, each inactive molecule is in the form of a closed-circle which may be opened by cleavage or splicing-out of a stretch of nucleotides, by a catalytically active initiation ribozyme. Activated (open) ribozymes then open and activate other such closed-circle molecules of the catalytic system.

In an analogous manner to that described above for the said another above second embodiment, each single species of the composite molecule may comprise a ribozyme positioned in an orientation which prevents self-cleavage of the adjacent cleavable nucleic acid sequence, for example, by placing the sequence immediately adjacent to the ribozyme.

The fact that there are no intervening sequences between the ribozyme and the cleavable sequence sterically inhibits the cis cleavage. (The cleavable sequence may also have an inversed orientation, and cis cleavage will thus not be possible). However, released ribozyme may approach the nucleic acid sequence in a correct orientation, and cleave it, thereby releasing more ribozymes to the medium. In order to prevent spontaneous trans cleavage of non-released ribozymes, it is possible to ensure spatial separation similarly as indicated above.

Detection of the presence of activated ribozymes in the catalytic system may take various forms depending on the type of catalytic activity of the ribozyme. Where, for example, the activity is cleavage or spliced out, a label may be linked to the part to be cleaved or spliced out and detection of such freed label is then an indication of the presence of the catalytically active initiation ribozyme in the medium.

In some cases the activation of the ribozyme brings to a change in the distance between two regions of the ribozyme, such as where two distant regions are brought together by ligation or rearrangement, by splicing out of an interfering region, or wherein two initially adjacent regions are separated for example by opening of a closed circle. In such case it is possible to attach a fluorescent marker on one region of the ribozyme and a moiety, such as Rodamine which quenches the light emission from the fluoescent marker on the other region of the ribozyme. Rodamine has a quenching effect on the light emission of a fluorescent label when the two are adjacent and no such effect when the two are separated. By monitoring the change in light emission of the fluorescent label, it is possible to determine whether the two regions are adjacent (for example in the case of a closed-circle inactive ribozyme) or separated (when the ribozyme has been opened and activated).

The label may also be carried on a substrate which is not associated with the ribozyme and on which the catalytically active ribozyme may exert its catalytic activity. For example, the label may be carried on a nucleic acid sequence, which is cleaved or spliced-out as a result of a ribozyme's activity, whereby the label is released to the medium. The detection will in such a case be based on the presence of a free label in the medium.

The "ping-pong" cross activation, whether by cross-cleavage, cross-ligation, cross-splicing, cross rearrangement or alternating cycles of various catalytic actions, substantially amplifies the reaction resulting in a signal that indicating in a short time whether the initiation catalytically active ribozyme was present in the medium. While prior art amplification-detection methods such as PCR or LCR require several hours to be complete, the amplification-detection method of the invention is completed in a much shorter time period.

Where the catalytically active initiation ribozyme serves as a reporter ribozyme for the presence of other biomolecules, a detection system is required in which a catalytically active initiation ribozyme is generated only in the presence of the assayed biomolecule. This may be performed in one of the following embodiments, referred to herein as the "activation embodiment", the "transcription embodiment", the "assembly embodiment", and the "completion embodiment".

According to the activation embodiment, the initiation (reporter) ribozyme is a priori inactive. This inactivity may be a result of the absence of magnesium ions, which are required for the ribozyme's catalytic activity, from the medium; it may be a result of the presence of an inhibitory moiety in the medium; it may be a result of the presence in the medium of an oligonucleotide which hybridizes to sequence which is to be cleaved to either activate or free the ribozyme into the system, which cleavage is not possible as long as the sequence is double-stranded; etc. According to this embodiment, the ribozyme is linked to a recognition biomolecule which is capable of specifically recognizing and binding to the biomolecule which is to be assayed in the sample. For example, where the assayed biomolecule is an oligonucleotide sequence, the recognition biomolecule is the complementary sequence; where the assayed biomolecule is an enzyme, the recognition biomolecule may be a substrate; where the assayed biomolecule is an antigen, the recognition biomolecule may be an antibody which specifically interacts with the antigen; etc.

The ribozyme linked to the recognition molecule is then allowed to interact with the assayed biomolecules, and unbound ribozymes are then separated and washed away. Such separation can be carried out, on the basis of size difference between the complex of bound ribozymes and assayed biomolecules and that of free ribozymes; by, a priori, immobilizing the assayed biomolecules and then washing away free molecules of ribozymes; etc. After said separation, conditions are changed so as to activate the ribozyme, for example, by addition of lacking magnesium ions;

by modifying or removing the inhibitory moiety to stop its inhibitory activity; by melting the double-stranded non-cleavable sequence to a single stranded cleavable sequence; etc. Only if the assayed biomolecule is present, ribozymes which are bound thereto are retained, and only these retained ribozymes are activated by an appropriate change of conditions.

The transcription embodiment of the invention can be utilized where the assayed biomolecule is a nucleic acid sequence. The detection phase of this embodiment can be carried out generally as described in Israel Patent Applications Nos. 105894 and 111857 (and their counterpart PCT Publication Nos. WO 94/29481 and WO 96/17087) with the "triggering oligonucleotide" being said initiation ribozyme. The detection system of this embodiment comprises two oligonucleotide molecules, the first comprising a sequence complementary to the 5'-part of the assayed nucleic acid sequence and the second comprising a sequence complementary to the 3'-part of the assayed nucleic acid sequence. The first oligonucleotide molecule comprises upstream from the sequence complementary to the assayed biomolecule, a functional promoter, a sequence that codes for an initiation ribozyme sequence and a sequence that is capable of being cleaved by said detecting ribozyme (also essentially a DNA sequence). The second oligonucleotide molecule comprises, downstream from the complementary 3'-part of the assayed sequence, a triggering oligonucleotide template, the transcriptional product of which is capable of triggering transcription of sequences of initiation ribozymes as will be explained in detail hereinafter.

If the assayed biomolecule is not present in the test sample, then the triggering oligonucleotide sequence is not transcribed, since only presence of the assayed biomolecule brings together the two molecules required to produce the appropriate template of said triggering oligonucleotide sequence: namely the first oligonucleotide molecule carrying the functional promoter and the second oligonucleotide molecule carrying the triggering oligonucleotide template. If the assayed biomolecules are present, and in the presence of transcription system, the triggering sequence is produced and in turn is able to bring about production of transcripts containing initiation ribozyme linked to a sequence capable of being cleaved thereby. After self-cleavage, these transcripts release to the medium catalytically active initiation ribozyme.

According to the assembly embodiment of the invention, also appropriate in cases where the assayed biomolecule is a nucleic acid sequence, the detection system comprises a third oligonucleotide, comprising a sequence complementary to the 5'-portion of the assayed nucleic acid sequence, and a fourther oligonucleotide comprising a sequence complementary to the remaining, 3'-portion of the assayed nucleic acid sequence. Each of these oligonucleotides comprises also one portion (for example, half) of a ribozyme and both parts together constitute a full, functionally active ribozyme. In accordance with this embodiment, the function of the assayed nucleic acid sequence is to bring these two oligonucleotides together, thus yielding a functionally active initiation ribozyme. Thus, in the presence of an assayed nucleic acid sequence in the sample, the functional initiation ribozyme will be generated which could then be detected in the catalytic system of the invention.

In accordance with the completion embodiment of the invention, the detection system comprises a seventh oligonucleotide and the assayed sequence, complexes with the seventh oligonucleotide to yield a catalytically active initiation ribozyme. For example, the assayed sequence may form part of the catalytic core of the ribozyme. Thus, in accordance with this embodiment, the ribozyme is a priori incomplete, and only in the presence of the assayed sequence it becomes a complete, catalytically active ribozyme which may then be detected in the catalytic system.

The assayed sequence may complete the ribozyme by hybridizing at its 3'-end to a sequence on one side of the ribozyme's missing portion, and by hybridizing at its 5'-end to a sequence on the other side of the ribozyme's missing portion, thus bridging the missing portion and creating a functional initiation ribozyme.

The assayed sequence may also be able to complete the ribozyme's missing portion by "reverse exon splicing", wherein the assayed sequence is inserted into the ribozyme through suitable cleavage and ligation reactions. Said "reverse exon splicing" may be carried out by other ribozymes present in the medium.

In order to decrease the "noise" level of the method of the invention and decrease false positive results, it is possible to combine two or more embodiments of the invention to doubly ensure that no catalytically active initiation ribozymes are produced in the absence of assayed biomolecules. For example, it is possible to combine the assembly and activation embodiments of the invention, whereby catalytically active ribozymes will be generated only as a result of two accumulative conditions: assembly of a full ribozyme from its two parts in a magnesium-less mixture, and after washing away free incomplete ribozymes, activating of the full ribozyme by addition of magnesium ions.

The ribozymes used in most embodiments of the detection system of the invention are in most cases universal, i.e. the same ribozyme can be used to detect different assayed biomolecules since the specificity is acquired by the attached recognition biomolecule (in the activation embodiment), or by the first and second oligonucleotide molecules (in the transcription embodiment) or by third and fourth oligonucleotide sequences (in the assembly embodiment). The fifth oligonucleotide in the case of the completion embodiment of the invention has to be tailor made for each specific nucleic acid to be assayed, since the sequence recognizing the assayed sequence is part of the ribozyme itself.

The present invention also provides reagents required for carrying out the above method as well as a kit comprising said reagents.

In the following the invention will be described with reference to some non-limiting drawings and examples:

In the drawings various symbols are used which in the context of the present invention have the following meanings:

| | |
|---|---|
| Straight line (___) | DNA strand |
| Wavy line (~~) | RNA strand |
| A, B, C, etc. . . . | sequences in the coding strand of a DNA |
| A', B', C', etc. . . . | sequences in the complementary non-coding DNA strand |
| a, b, c, etc. . . . | RNA sequences |
| a', b' c', etc. | RNA sequences complementary to a, b, c |
| \\\\\ | immobilization on a solid support |
| * | detectable label |
| ⊠ | inhibitory moiety. |

BRIEF DESCRIPTION OF THE DRAWINGS

FIG. 2(a) and 2(b) show a catalytic system in accordance with an embodiment of the invention comprising one species of composite molecule activated by cross-cleavage or cross-splicing: wherein the ribozyme is in the form of a closed circle (FIG. 2(a)); wherein the ribozyme requires splicing for becoming active (FIG. 2(b));

FIG. 6 shows a detection system in accordance with the transcription embodiment of the invention;

DESCRIPTION OF SPECIFIC EMBODIMENTS

Catalytic System

Figure 1:
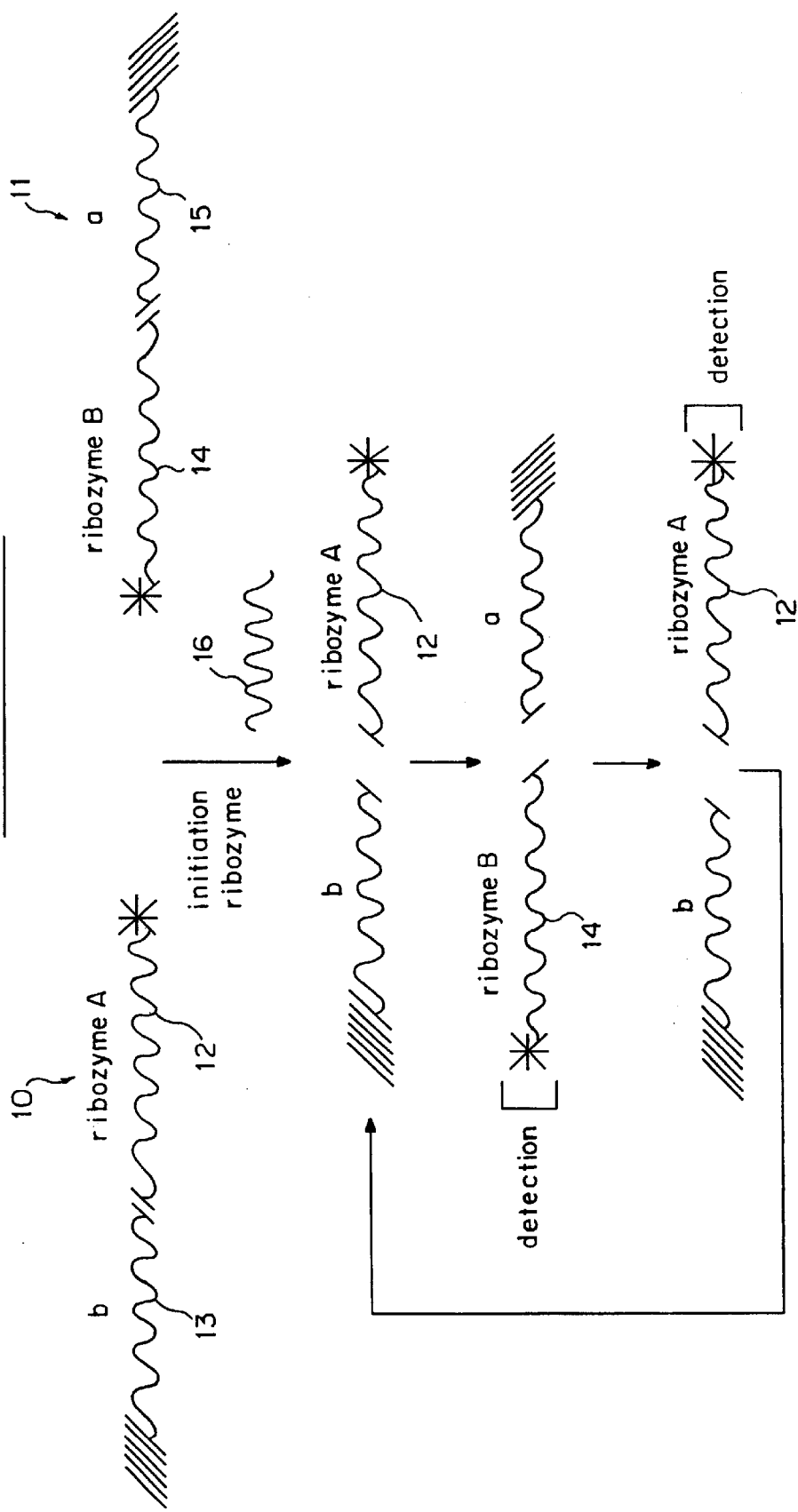
FIG. 1 shows an embodiment of the catalytic system of the invention comprising two species of composite molecules activated by cross-cleavage.

Reference is first made to FIG. 1 showing one manner of constructing the catalytic system of the invention. The catalytic system comprises two species of composite molecules 10 and 11. Composite molecule 10 comprises one type of labelled ribozyme which will be denoted ribozyme A (12) linked to an RNA sequence denoted b (13). Composite molecule 11 comprises another type of labelled ribozyme which will be denoted ribozyme B (14) and an RNA sequence a (15). Ribozyme B in molecule 11 is capable of cleaving sequence b in molecule 10 and ribozyme A in molecule 10 is capable of cleaving sequence a in molecule 11. Initially molecules 10 and 11 are not able to interact since each is immobilized to a distinct site of the reaction vessel. Initiation ribozyme 16 is also capable of cleaving sequence b in molecule 10.

If initiation ribozyme is present in the reaction mixture then sequence b is cleaved releasing free ribozyme A (12) to the reaction mixture. Free ribozyme A (12) is able to diffuse within the reaction vessel to cleave molecule 11, thus releasing to the reaction mixture free ribozyme B (14). Free ribozyme B (14) is again able to migrate through the reaction vessel to cleave molecule 10 to release again free ribozyme A (12) and the cycle is repeated again and again in a positive-feedback manner. Since both ribozyme A and B are labelled, detection of either or both in the supernatant indicates the presence of initiation ribozyme 16 in the reaction mixture.

The following is an example of molecule 10 comprising a ribozyme 12 of the type hammerhead linked to sequence 13 which is then labelled at 3'-end by biotin: (Capital letters: 2'-O-methylated; small letters: RNA)

5'CCA cugauga gGCC GAAA GGCc gaa acGUguc CGU AAA(SEQ ID NO:1)

The following is an example of molecule 11 comprising another ribozyme 14 of the type hammerhead which is capable of cleaving seqeuence 13 present in molecule 10. Ribozyme 14 is linked to sequence 15 capable of being cleaved by ribozyme 12 of molecule which is then labelled at its 3'-end by biotin: (Capital letters: 2'-O-methylated; small letters: RNA)

5'-GAG ACG cugauga gGCC GAAA GGCc gaa acAC guc UGG AAA(SEQ ID NO:2)

Although ribozymes A and B are referred to as different ribozymes and sequences a and b are referred to as different sequences, both the ribozymes and sequences may be actually identical. In such a case self-cleavage in each molecule 10 or 11 is avoided by linking the ribozyme to its attached sequence in such a proximity which does not enable cleavage in cis, while free ribozymes are able to cleave composite molecules in trans.

This can be done by linking the ribozyme immediately adjacent to its potentially cleavable sequence. This is because the ribozyme should be spaced from its potentially cleavable sequence by several nucleotides for efficient cleavage to take place. Therefore, when the ribozyme in the composite molecule is linked directly with no spacing to the cleavable sequence, there is no possibility of cis cleaving and the sequences can be cleaved only in trans while enabling only cleavage in trans.

Reference is now made to FIG. 2(a) which shows another alternative where only one species of composite molecules is present in the reaction vessel. The catalytic system comprises a single species of molecules 17', each comprising a ribozyme C' (18') and a cleavable sequence c' (19'). The molecule 17' is in the form of a closed circle and thus ribozyme 18' is initially inactive.

If catalytically active iniation ribozyme 16' is present in the media, it is able to cleave the sequence c' and open the ribozyme to become active. Open ribozyme 18' can in turn open, by cleavage, additional composite molecules 17' turning them active. Detection can be carried out by using a fluorescent label (F) and Rodamine (Rd). When the two are adjacent as in the closed molecule the light emission of the fluorescent label is quenched and when they are separated, as in the open molecule sequence, the light emission of the fluorescent label becomes stronger.

Figure 2B:
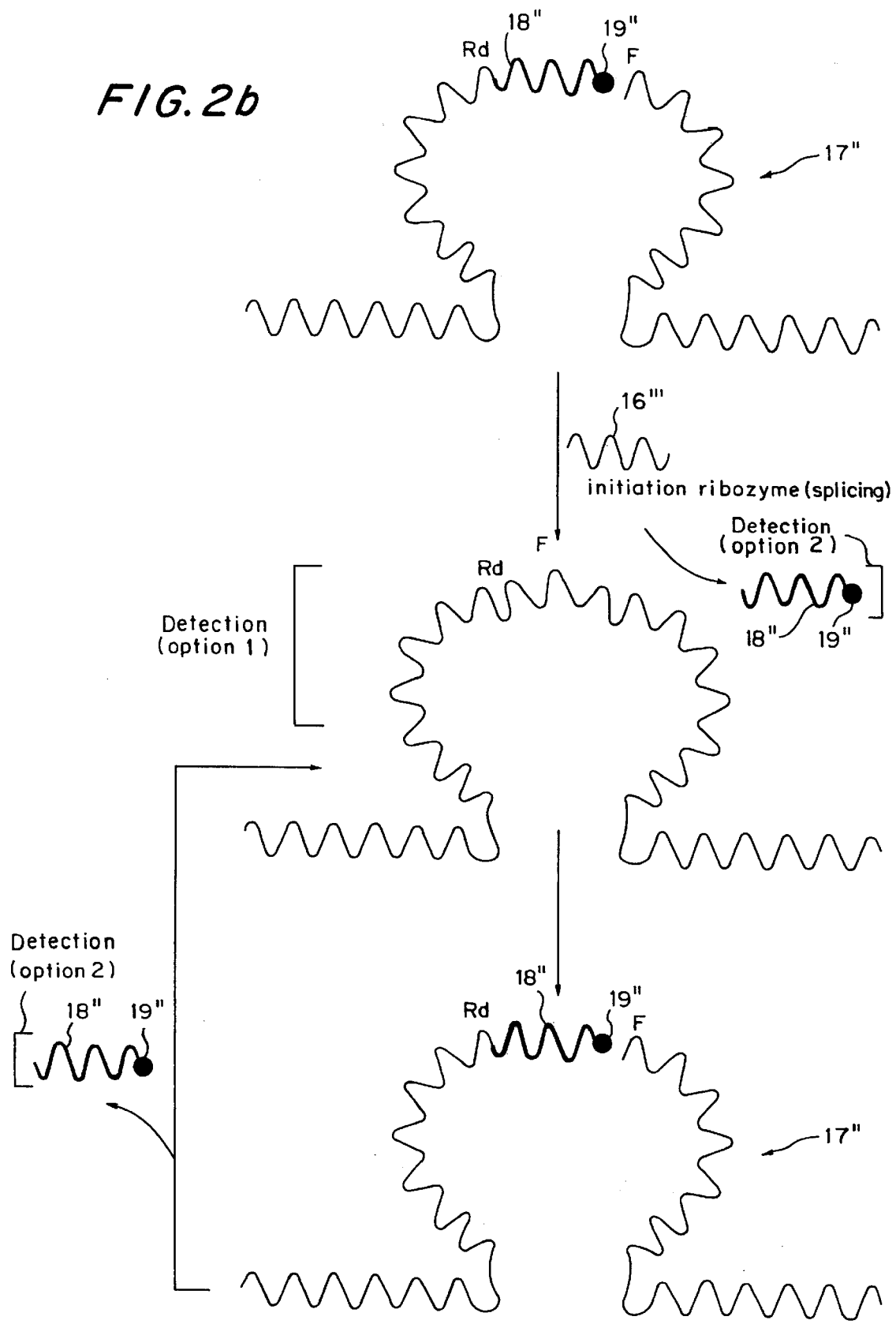

Reference is now made to FIG. 2(b) which shows yet another alternative for the catalytic system comprising only a single species of composite molecule. Ribozyme 17' has in its core region an extra nucleotide sequence 18" which renders the ribozyme inactive. At the terminal of the extra sequence is a blocking group 19 which does not allow spontaneous ligation of the open end.

Initiation ribozyme 16, which has the catalytic activity of splicing is capable of both cleaving out extra sequence 18 and blocking group 19 and then of ligating the free ends to give a functional ribozyme. Functional ribozyme is then capable of splicing other ribozymes in the reaction medium causing an amplification of the reaction. Detection according to one option (Option 1) is carried out essentially as described in FIG. 2(a), but in this case, initially the Rodamine (Rd) at the fluorescent group (F) are separated and only upon activation of the ribozyme they become adjacent, so that active ribozyme is detected by quenching of light emission. According to the second mode of detection (Option 2) the spliced out group comprising free extra sequence 18 and blocking group 19 carries a detectable label.

The advantages of the mode of FIG. 2(b) resides in a very low "noise" level since in order for an inactive ribozyme to become spontaneously active (not in the presence of an initiation ribozyme) two spontaneous occurrences must happen spontaneous cleavage (at a probability of $10^{-6}$/min in 10 mM MgCl at physiological pH and at a temperature of 37° C.) and spontaneous ligation (at a probability of $10^7$/min) giving a very low probability for spontaneous activation ($10^{13}$/min).

The label attached to either or both ribozymes A, B or C (FIG. 1) may be any detectable label known in the art such as a radioisotope, a fluorescent label, an enzyme which in the presence of a substrate is capable of producing a color reaction, etc.

FIG. 3 shows various manners in which the two composite molecules 10 and 11 of the first embodiment are positioned so as to avoid mutual interaction but allow interaction between free ribozymes 12 and 14 and composite molecules. It should be understood that the same principles apply also to the other manner for constructing the catalytic system of the invention, i.e. where only one species of composite molecule is present, represented in FIG. 2.

Figure 3A:
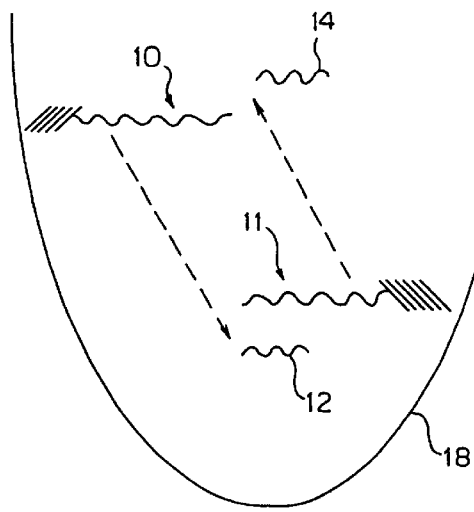
FIG. 3 shows various manners in which composite molecules can be separated from one another: by immobilization to distinct sites of the reaction vessel (3A); by linkage to large beads (3B); by linkage to charged moieties (3C); and by placing each species of composite molecules at opposite sides of a porous membrane (3D)

In FIG. 3(A) molecules 10 and 11 are immobilized onto distinct and separate sites of the reaction vessel 18 while ribozymes 12 and 14 diffuse freely in the reaction mixture.

Figure 3B:
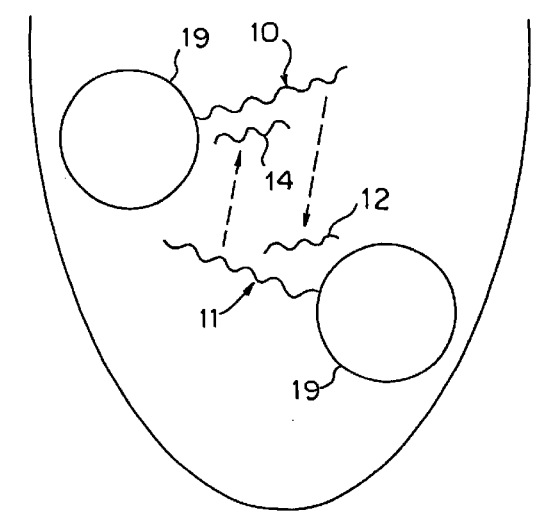

FIG. 3(B) shows molecules 10 and 11 which are immobilized onto beads 19 the size of which prevents interaction between said molecules. However, free ribozyme 12 and 14 are able to diffuse freely in the reaction mixture and interact with the composite immobilized molecules.

Figure 3C:
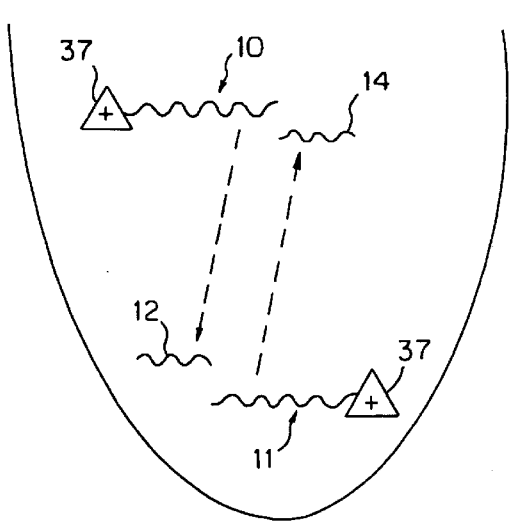

FIG. 3(C) shows another example of separating composite molecules wherein composite molecules 10 and 11 are attached to charged moieties bearing the same charge 37. The electrical rejection between their attached moieties eliminates the possibility of interaction between molecules 10 and 11. However, free ribozyme 12 and 14 which are essentially uncharged are able to interact with the composite molecule.

Figure 3D:
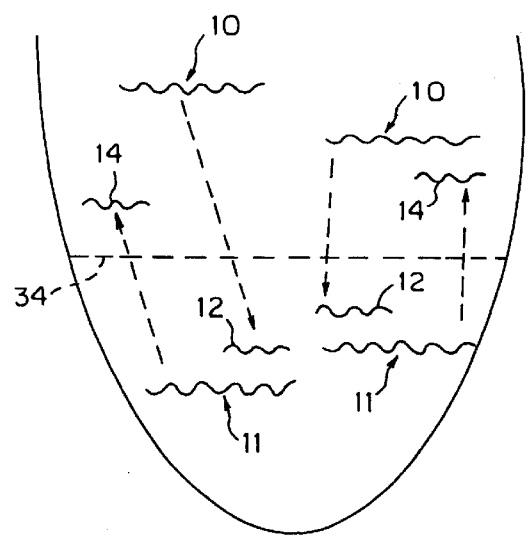

FIG. 3(D) shows yet another example of separating the composite molecules 10 and 11 by placing them at opposite ends of a porous membrane 34 which serves as a sieve, blocking passage of large molecules 10 and 11 while allowing passage of the smaller free ribozymes 12 and 14.

Another manner for ensuring that the two composite molecules 10 and 11 do not interact is by the use of blocker molecules which are complementary to a specific sequence rendering it double stranded. According to this manner, composite molecule 10 comprises a blocker molecule which renders the cleavable sequence b and part of the catalytic region of ribozyme A double stranded. In the partially double stranded composite molecule 10, the ribozyme is not active due to the fact that its catalytic region is double stranded. Composite molecule 11 is blocked in a similar manner. If initiation ribozyme is present in the reaction mixture, it displaces a part of the blocker molecule present on the composite molecule 10, and then the initiation molecule is able to cleave sequence b. Once sequence b is cleaved ribozyme A is also rendered active since the partially displaced blocker molecule completely falls off composite molecule 10 turning its catalytic region to become single stranded and active. Active ribozyme A then displaces the blocker molecule of composite molecule 11 in a similar manner as described above cleaving the cleavable sequence a, turning Ribozyme B single stranded and active. Ribozyme B then activates composite molecule 10 in a similar manner to the activation of the initiation ribozyme described above, and cross activation of the two composite molecules can then proceed.

Figure 8:
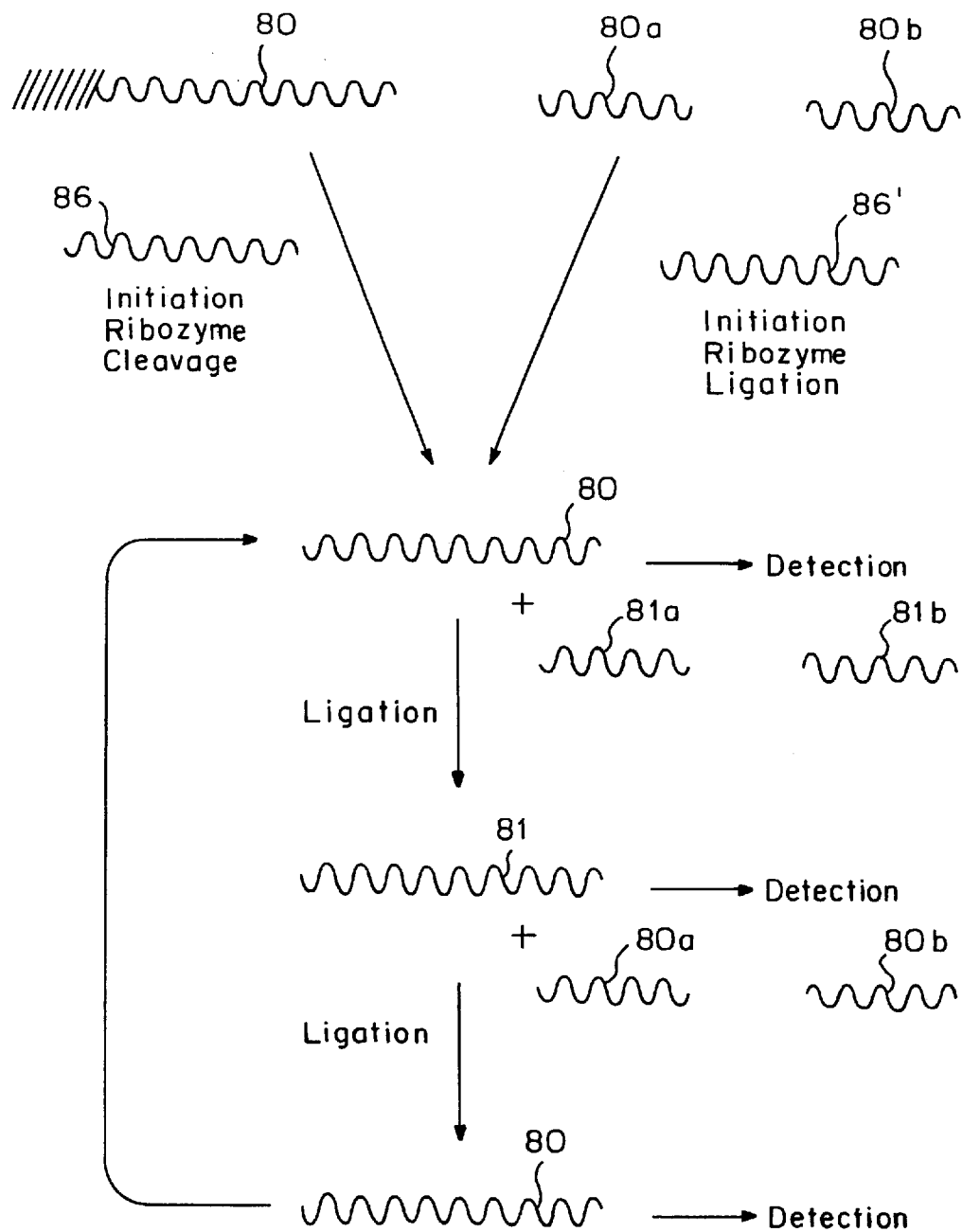
FIG. 8 shows an example of the catalytic system of the invention comprising two species of ribozymes activated by cross-ligation.

Reference is now made to FIG. 8 which shows another alternative for constructing the catalytic system of the invention. The catalytic system comprises two species of ribozymes 80 and 81 which are active when fully assembled but are inactive when separated to their parts 80a, 80b and 81a, 81b, respectively. Full ribozyme 80 is capable of ligating ribozyme parts 81a and 81b to produce a full and active ribozyme 81. Full ribozyme 81 is capable of ligating ribozyme parts 80a and 80b to produce a full and active ribozyme 80, so that cross-activation proceeds by cross-ligation.

Initiation ribozyme 86 or 86' is capable of creating a full and active ribozyme 80 either by cleaving a full but immobilized ribozyme from a location wherein it is spatially separated from ribozyme parts 81a and 81b, for example, in one of the manners specified in FIG. 3 (FIG. 8 top left) or by being able to ligate parts 80a and 80b to form the full and active ribozyme 80 (FIG. 8 top right).

Detection System

Where the method of the invention is to be used to aid in the detection of biomolecules other than ribozymes, the invention includes also a detection system capable of producing catalytically active initiation ribozyme only in the presence of the assayed molecule.

Figure 4:
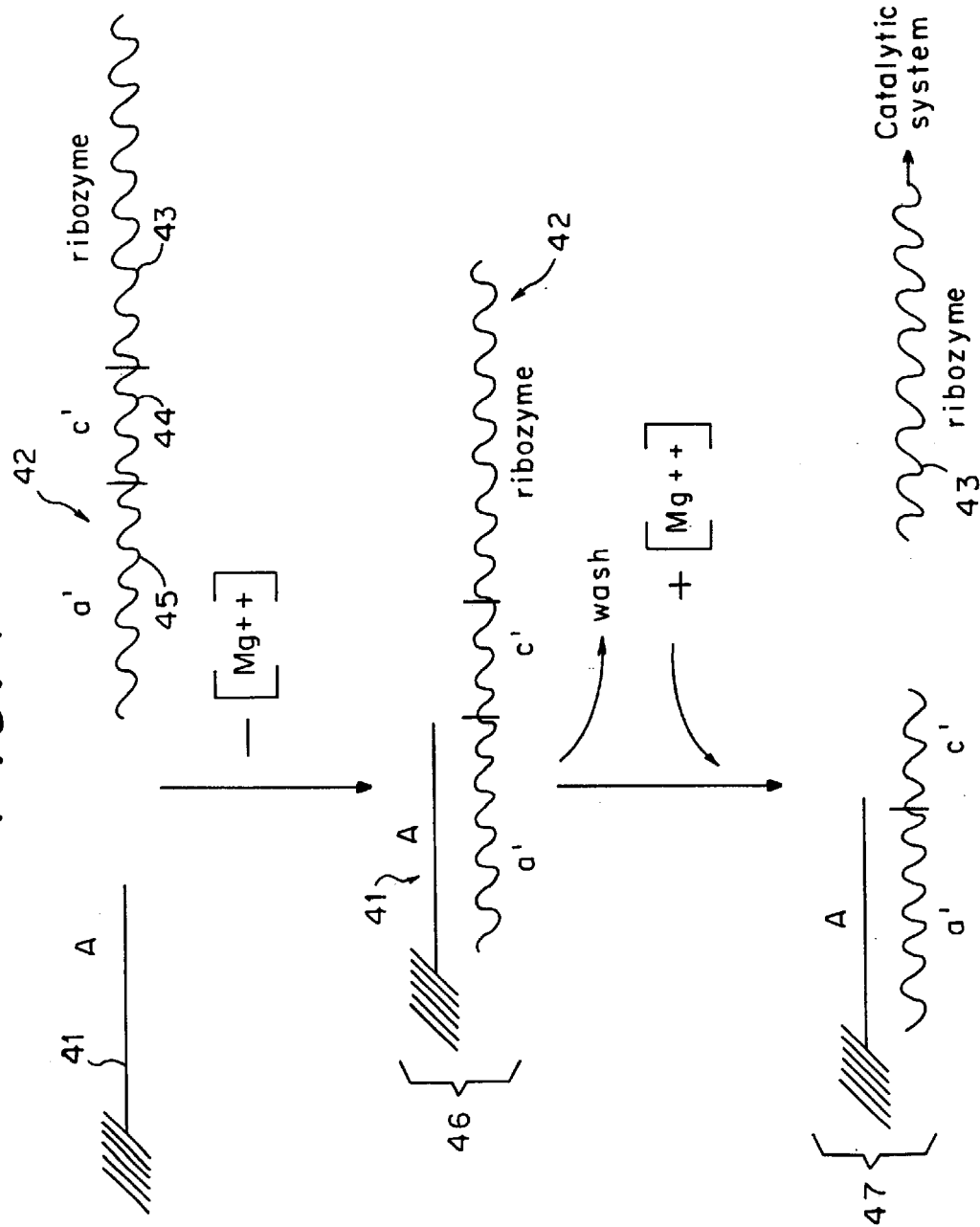
FIG. 4 shows an example of the detection system according to the activation embodiment of the invention wherein the ribozyme is activated by addition of magnesium ions.

FIG. 4 shows one example of the activation embodiment of the invention. In this example, the assayed biomolecule is an immobilized nucleic acid sequence A (41) for example a DNA sequence. Immobilization can be carried out in accordance with any method known in the art, for example, with the aid of a cross-linking agent or by trapping the assayed nucleic acid molecule between two porous membranes which permit passage of smaller molecules. Where the assayed biomolecule is a protein it can be immobilized onto beads carrying appropriate trapping agents, such as suitable immobilized antibodies, directed against regions which are not required for detection, etc. Alternatively, the assayed biomolecule can be immobilized onto a nitrocellulose sheet and another protein, such as albumin, should then be applied onto the nitrocellulose sheet in order to saturate all the sheets' vacant locations and avoid, in the next step, non-specific absorption.

The detection system also comprises first complex molecule 42 comprising ribozyme 43, linked to cleavable sequence c' (44) capable of being cleaved by active ribozyme, and further comprises sequence a' (45) complementary to the assayed sequence A (41). Ribozyme 43 does not self-cleave since molecule 42 is kept in magnesium-less reaction mixture which eliminates the ribozymes catalytic activity. This can be done, for example, by keeping complex molecule 42 in a magnesium-less EDTA-containing reaction mixture.

An example of ribozyme 43 linked to the cleavage sequence C' (44) of the type hammerhead (Capital letter: 2'-O-methylated; small letters: RNA; over- and underlined: DNA)

(SEQ ID NO: 3)

5'-<u>GCAACAGTGGAGGAAAGCC</u> UACguc UGG UACGU CCA cugauga gGCC GAAA GGCc gaa acGUAGU AAA Molecules 41 and 42 are allowed to hybridize to give immobilized hybrid 46. Free molecules 42 are washed away, and to the immobilized hybrid 46 are added magnesium ions in a concentration sufficient to activate ribozymes. In the presence of such a concentration of magnesium ion ribozyme 43 is able to cleave sequence c', thus releasing itself to the reaction mixture while leaving immobilized cleaved hybrid 47. Free and catalytically active ribozyme 43 can serve as the initiation ribozyme in the catalytic system.

Figure 5:
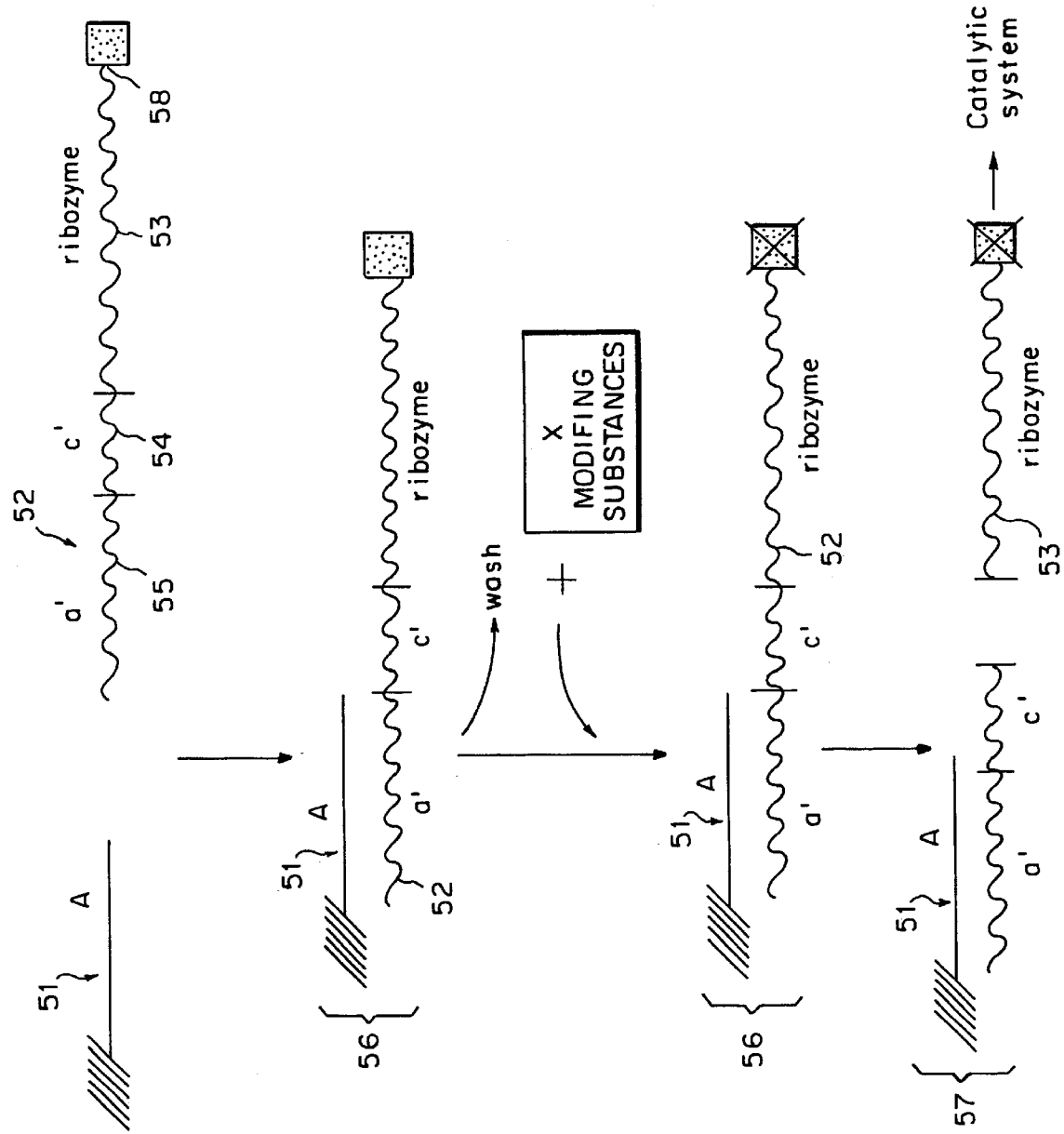
FIG. 5 shows another example of the detection system according to the activation embodiment of the invention wherein the ribozyme is activated by modification of an inhibitory moiety.

FIG. 5 shows another example of the activation embodiment of the invention. Assayed biomolecule 51, which comprises nucleic acid sequence A, for example a DNA sequence is immobilized as described above. The detection system comprises a second complex molecule 52 comprising ribozyme 53 linked to sequence c' (54) which can be cleaved by catalytically active ribozyme and sequence a' (55) complementary to sequence A in the assayed biomolecule. The complex molecule also comprises an inhibitory moiety 58 which, while present in its unmodified form, inhibits the catalytic activity of ribozyme 53. An example of an inhibitory molecule is a nucleic acid sequence complementary to part of the ribozyme. In the presence of such a sequence, the ribozyme folds to an inactive three-dimensional form.

Molecules 51 and 52 are allowed to hybridize to give immobilized hybrid 56, and free molecules 52 are washed away. To separate hybrid 56 are added modifying substances which are able to interact with the inhibitory moiety 58 and modify it to an un-inhibiting form. For example, where the inhibitory moiety is a nucleic acid sequence which causes folding of the ribozyme, the modifying substance may be a sequence complementary to the inhibitory moiety, which hybridizes and blocks the inhibitory moiety, thus allowing the ribozyme to refold to its active form. Alternatively, the modifying substances may be substances able to remove or cleave the inhibitory moiety, thus terminating its inhibitory action. Active ribozyme is then able to cleave sequence c, thus releasing itself from immobilized cleaved hybrid 57. Catalytically active free ribozyme 53 then serves as the initiation ribozyme in the catalytic system.

Figure 9:
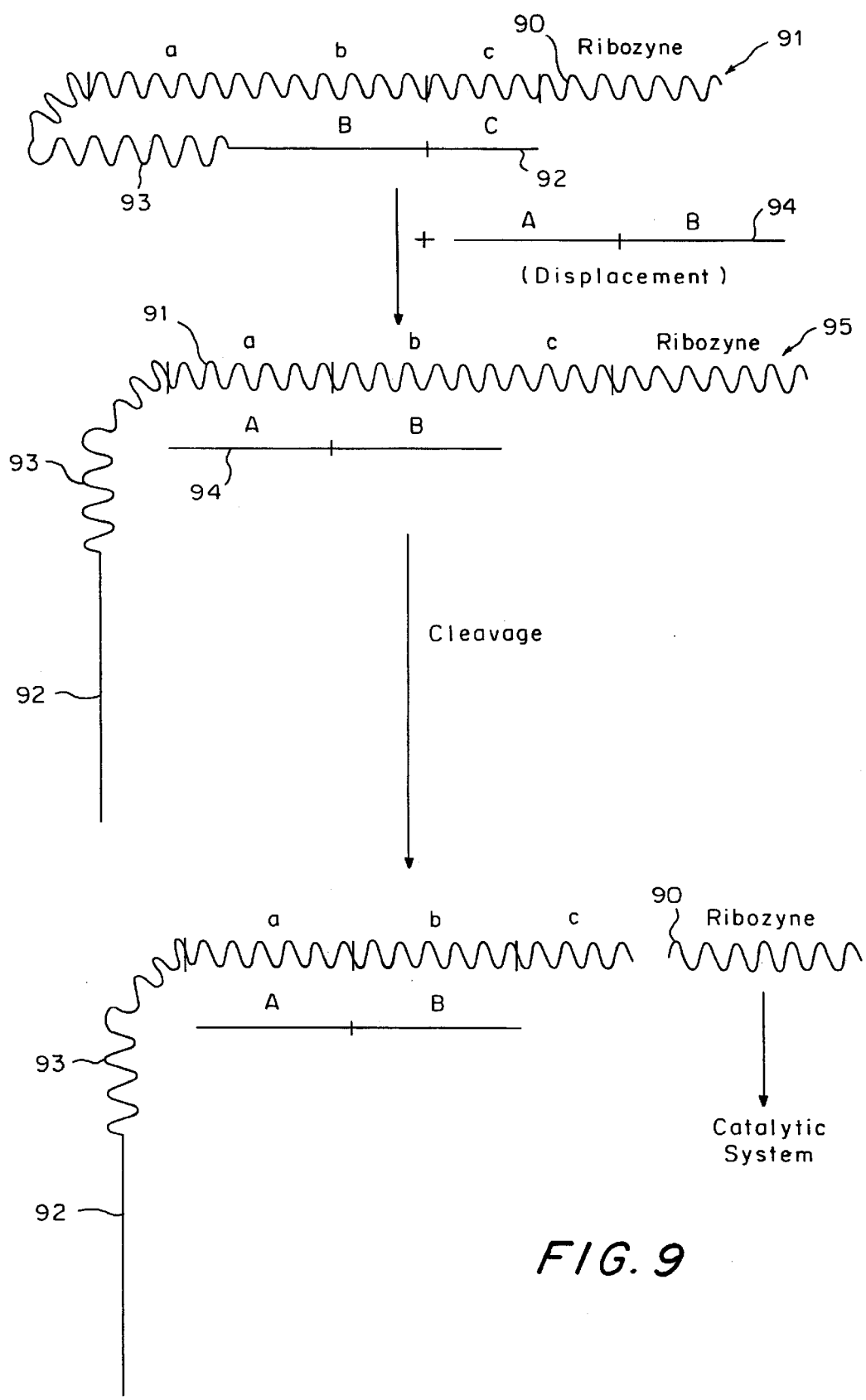
FIG. 9 shows yet another example of the detection system according to the activation embodiment of the invention wherein the ribozyme is activated by rendering the cleavable sequence single stranded.

Reference is now made to FIG. 9 which shows another example of the activation embodiment of the invention. Molecule 91 comprises the sequence of the initiation ribozyme 90, attached to sequence c, cleavable by the ribozyme, and to sequence a and b which are capable of hybridizing with the assayed biomolecule being, for example the assayed DNA sequence of molecule 94. Molecule 91 further comprises blocker DNA sequence 92 which comprises sequence B and C, capable of hybridizing to sequences b and c of molecule 91, respectively, to give a double-stranded structure. Blocker DNA sequence 92 is linked via linker sequence 93. The ribozyme 90 is not capable of cleaving sequence c since its sequence region is double stranded (through hybridization to blocker sequence 92).

The assayed molecule 94 is then introduced to the reaction mixture. If the assayed biomolecule is complementary to a and b of molecule 91, then blocker sequence 92 is displaced by the assayed molecule 94 to give hybrid molecule 95. In hybrid molecule 95, the cleavable sequence c is single stranded enabling the ribozyme to cleave it and thus to be freed to the reaction mixture as a catalytically active ribozyme 96 which serves as the initiation ribozyme in the catalytic system.

According to this embodiment conditions such as temperature, the length of the part of the recognition biomolecule b which is double stranded, etc. must be chosen with care so that the assayed molecule is able to displace blocker molecule 92 essentially only if the assayed biomolecule sequences A and B are perfectly matched to recognition sequences a and b.

Reference is now made to FIG. 6 which shows the transcription embodiment of the detection system of the invention appropriate where the biomolecule is a nucleic acid sequence. According to this specific embodiment a correct DNA template, which eventually brings to the transcription of initiation ribozyme, is assembled from its parts only in the presence of the assayed nucleic acid sequence. The detection system comprises a first oligonucleotide molecule 61, being essentially DNA, comprising from 3'→5'; a double-stranded promotor, a sequence R coding for the complementary sequence of the initiation ribozyme, a sequence C coding for a sequence cleavable by a catalytically active ribozyme, and a sequence $D_1$ complementary to the 5'-part of the assayed nucleic acid sequence. The detection system further comprises second oligonucleotide molecule 62, being essentially DNA comprising from 3'→5': a sequence $D_2$ complementary to the 3'-part of the assayed nucleic acid sequence and a triggering oligonucleotide template (TRIG). If assayed nucleic acid sequence 63 is present, and under appropriate hybridization conditions, sequence $D_1$ of molecule 61 and sequence $D_2$ of molecule 62 hybridize with sequences $D_1'$ and $D_2'$, respectively, of the assayed nucleic acid sequence to give hybrid 64.

In the presence of transcription system non-template strand oligonucleotide 65 is produced, comprising from 3'→5': triggering oligonucleotide sequence trig, $d_2'$ and $d_2'$ sequences, sequences c' r', complementary with those of the cleavable nucleic acid sequences and the initiation ribozyme, respectively.

To the reaction mixture are added molecules of back promotor construct 66 comprising a single-stranded DNA promotor linked to a sequence capable of hybridizing with the oligonucleotide triggering sequence TRIG. Under appropriate conditions the back promotor construct 66 hybridizes with molecule 65 to give hybrid 67. In the presence of a DNA polymerase the single-stranded promotor is completed to give a functional double-stranded promotor in hybrid 68.

Hybrid 68 can serve, in the presence of transcription reagents, as a template for the production of final oligonucleotide transcript 69 comprising from at its 5'-end: an initiation ribozyme sequence r and a cleavable sequence c capable of being cleaved by said ribozyme.

The ribozyme r cleaves cleavable sequence c thus releasing itself to the surrounding medium in the form of free ribozyme 70. Free ribozyme 70 can serve as the catalytically active initiation ribozyme in the catalytic system.

Figure 7A:
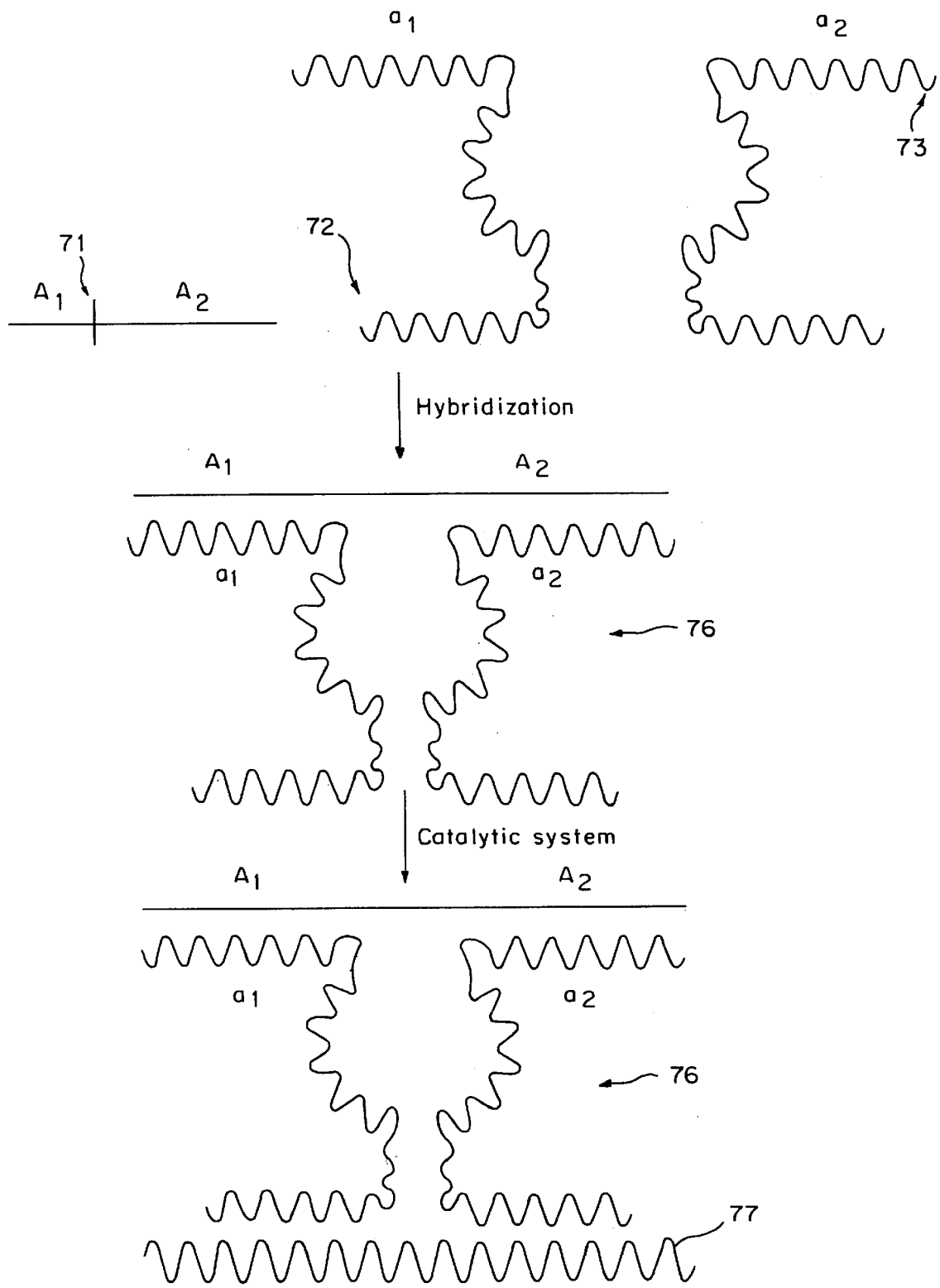
FIG. 7(a) and 7(b) show a detection system in accordance with the assembly embodiment of the invention; where the recognition sequence of the ribozyme hybridize to the assayed nucleic acid sequence (FIG. 7(a)); or where the opened stemp-II of the ribozyme hybridizes with the assayed sequence (FIG. (b))

One mode of the assembly embodiment of the invention is shown in FIG. 7(a). The detection system comprises assayed biomolecule 71, comprising a nucleic acid sequence $A_1A_2$. In addition, the detection system comprises a part of a ribozyme 72, comprising oligonucleotide sequence $a_1'$, complementary to sequence $A_1$ and another part of a ribozyme 73 comprising oligonucleotide sequence $a_2'$ complementary to sequence $A_2$. The parts of ribozyme 72 and 73 together constitute a complete ribozyme if the two parts are assembled.

If assayed molecule 71 is present in the medium, it can hybridize to $a_1$ of ribozyme part—72 and $a_2$ of ribozyme—part 73 bringing the two parts together to form functional ribozyme-assayed sequence hybrid 76, which may serve as an initiation ribozyme in a catalytic system, for example, by cleaving molecule 77, which cleavage may be required to initiate the amplification cascade in the catalytic system.

Figure 7B:
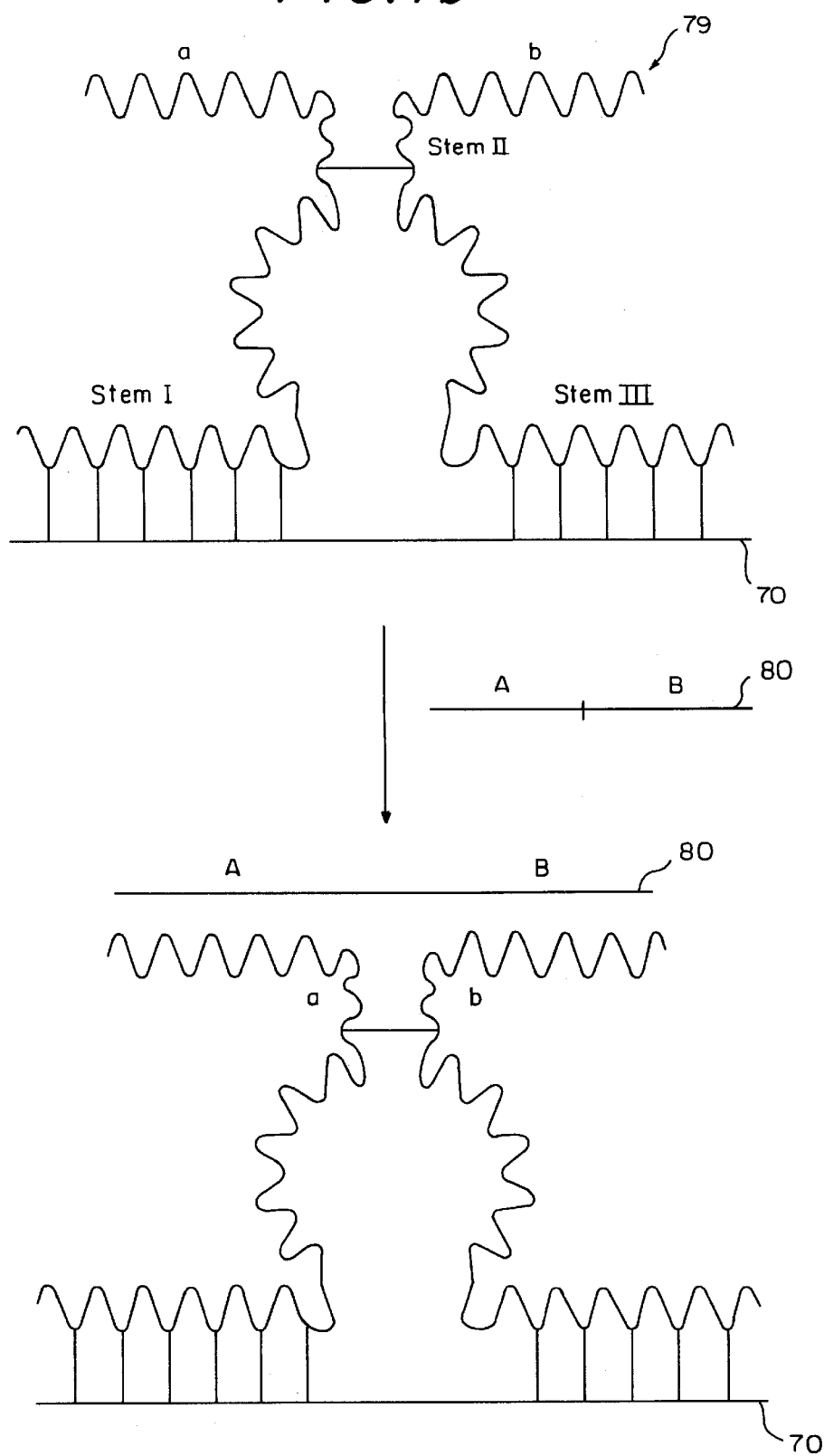

Another mode of the assembly mode of the invention is shown in FIG. 7(b).

Ribozyme 79 of the hammer-head type has been constructed in which Stem-II has been shortened to have only one complementary nucleotide (represented by one line in the FIG. 2b) and the remaining portion of the stem have been opened to give arms a and b. Ribozyme 79 is capable of hybridizing with sequence 70 to form Stems I and III and then perform the catalytic activity, for example, cleavage of sequence 70.

However, a priori ribozyme 79 is incapable of cleaving the cleavable sequence 70 since its Stem-II is open and inactive. Arms a and b of the opened core have been constructed to be complementary to sequences A and B of the assayed sequence, for example, DNA sequence 80.

In the presence of assayed DNA sequence 80, the arms a and b of the stem-II ribozyme 79 are hybridized to the assayed sequence to produce a fully double-stranded Stem-II and thus the ribozyme becomes catalytically active and can serve as an initiation ribozyme in a catalytic system where, for example, cleavable sequence 70 is part of an enzyme in the catalytic system which requires cleavage for its activation.

EXAMPLES

Example 1
Detection of an Assayed Nucleic Acid Sequence Using a Ribozyme with an Open Stem-II Ribozyme HH8 was dissected in to two parts at the loop of stemp-II. Each of the two ribozyme halves of HH8 (HH8-3 and HH8 5) has a different additional 17 bases tail sequence complementary to the LAMTAR0 DNA target molecule. In the presence of the target, the two halves are brought together and form an active ribozyme. In the LAMTAR0 target the two sequences complementary to the ribozyme halves are continuous. In the other LAMTAR molecules (LAMTAR1 through LAMTAR4) the two sequences are separated by 1 to 4 non-complementary bases respectively. The ribozyme substrate is SB8-24 which contains the sequence recognized by HH8.

(a) Method
 1. Sequences:

Oligodeoxyribonucleotides were synthesized on an Applied Biosystem 381A DNA synthesizer according to the manufacturer's recommended protocol. The Ampliscribe kit (Epicenter Technologies) was used for all RNA synthesis [$\alpha^{32}$ P] UTP [3000 Ci/mmol] was purchased from Rotem Industries Ltd., Israel.

DNA Targets:
  LAMTAR: 5'GCTCCGAGTCCACCTGCACGCCGACCAGTGCCGTGTTCGGGA 3'(SEQ ID NO:4)
  LAMTAR1: 5'GCTCCGAGTCCACCTGCACGCTCGACCAGTGCCGTGTTCGGGA 3'(SEQ ID NO:5)
  LAMTAR2: 5'GCTCCGAGTCCACCTGCACGCTTCGACCAGTGCCGTGTTCGGGA 3'(SEQ ID NO:6)
  LAMTAR3: 5'GCTCCGAGTCCACCTGCACGCTATCGACCAGTGCCGTGTTCGGGA 3'(SEQ ID NO:7)
  LAMTAR4: 5'GCTCCGAGTCCACCTGCACGCTATACGACCAGTGCCGTGTTCGGGA 3'(SEQ ID NO:8)

Underlined—complementary to ribozyme half;
 Bold—non-complementary additional sequence.
 RNA Transcripts:
  SB-24 (substrate for HH8): 5'GGUCACAAUGUCGGUCGAGUUCCA 3'(SEQ ID NO:9)
  HH8-3 (ribozyme half): 5'GGCGACCCUGAUGAGGCCGCGUGCAGGUGGACUCG 3'(SEQ ID NO:10)
  HH8-5 (ribozyme half): 5'GGAACACGGCACUGGUCGGGCCGAAACAUUAA 3'(SEQ ID NO:11)

Underlined—complementary to target.
 2. Preparation of RNA:

DNA oligonucleotides were synthesized according to (1) above. The oligonucleotides were purified by electrophoresis on 15% polyacrylamide 7M urea gel, UV-shadowed and eluted overnight at room temperature in 0.5M Tris-Cl (pH-7.0), 0.1% SDS and 0.1 mM EDTA. Eluted DNA was precipitated with 0.1 volumes of 3M sodium acetate and 3 volumes of ethanol, resuspended in 1 mM Tris-Cl (pH-7.0) and 0.1 mM EDTA and stored at −20° C. until use. Purified oligonucleotides were annealed to complementary non-template T7 RNA polymerase promoter oligonucleotide (TAA TAC GAC TCA CTA TAG G(SEQ ID NO:12)) in 20 mM each by incubating at 95° C. for 15 seconds and at 70"C., 60° C., 55° C., 50° C., 45° C., 40° C. and 37° C. for 5 min at each temperature. Transcription reaction mixture (50 ml) contained 2 mg of annealed DNA, 1× reaction buffer, 10 mM Dithiothreitol, 2 mM ATP, CTP and GTP, 1 mM UTP, 25 mCi [$a^{32}$ P] UTP and 1.1 mM MgCl$_2$. The mixture was incubated for 1 hr at 37° C. and then for 5 minutes at 80° C. to deactivate the enzyme. The RNA was precipitated as described. Transcripts were purified by electrophoresis on 15% polyacrylamide 7 M urea gel. RNA was located by autoradiography and eluted as described. Eluted RNA was precipitated as described, resuspended in 0.1× TE and counted in scintillation flour (Luma LSC).

3. Cleavage Reaction:

Reactions (10 ml) were normally carried out in the presence of 0.5 pmol ribozyme, 50 mM Tris-Cl (ph-7.5), 1 mM EDTA (pH-7.5), 0.05% SDS and 30 mM MgCl$_2$. The reactions were preincubated at 95° C. for 1 min in order to eliminate alternative RNA conformations which may have formed during storage at −20° C. The reactions were incubated at 37° C. for 1 hour and stopped by adding a dye solution containing 10 M urea and 10 mM EDTA and put on ice. The samples were denatured at 80° C. for 5 min and run on 15% polyacrylamide 7 M urea gel.

(b) Results

Figure 10B:
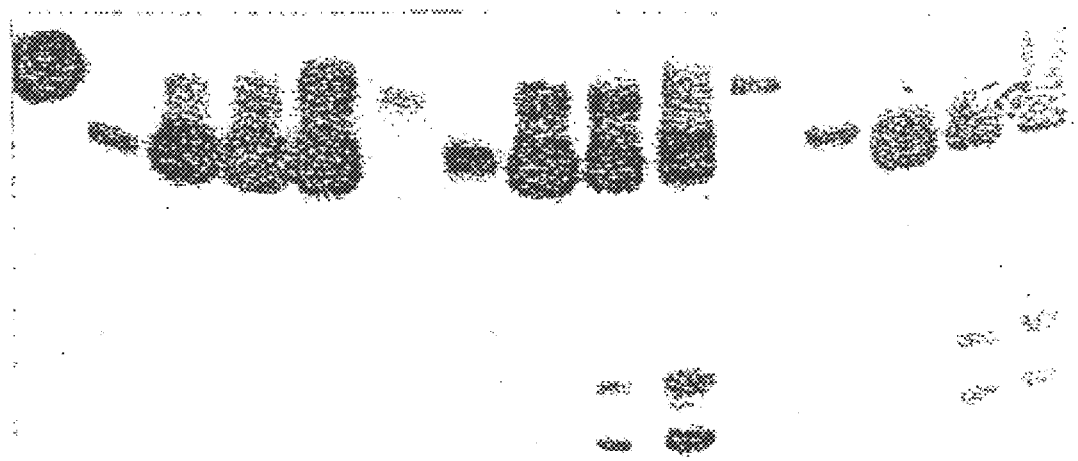
FIG. 10 shows the cleavage results of a detection system comprising the stem-II open ribozyme of FIG. 7(b)

The results of the polyacrylamide gel are shown in FIG. 10. Ribozyme without a target did not produce appreciable cleavage. When the target was added, enhanced cleavage resulted. The enhancement was greatest in LAMTAR4 Ribozymes tested.

Example 2
Catalytic System Comprised a Closed-circle Composite Molecule

The SLS-precursor ribozyme (Rz) is a circular Rz with 11 bp long stemp-II. The two recognition arms are connected in tandem with an extra cleavage base separating them. Therefore this robozyme has no activity, but serves as a template for active ribozymes. Once it has been cleaved, the "open" ribozyme becomes active (as shown schematically in FIG. 2(b)). In order to initiate the catalytic system an initiation ribozyme must be present. Spontaneous cleavage of RNA occurs at a rate of 1 event per $10^6$ molecules per minute in 30 mM MgCl, at 37° C. A circular ribozyme spontaneously cleaved at the cleavage site becomes active and is capable of serving as the trigger.

(a) Methods

1. Sequences:

Oligodeoxyriboniucleotides were synthesized on an Applied Biosystem 381A DNA synthesizer according to the manufacturer's recommended protocol. The Ampliscribe kit (Epicenter Technologies) was used for all RNA synthesis [$\alpha^2$ P] UTP [3000 Ci/mmol] was purchased from Rotem Industries Ltd., Israel.

The RNA precursor (SLS's) sequences were: 5' GGU CAG CAG UCG AA [Recognition arm I]x[Recognition arm III] CUG AUG AGA CUG CUG ACC A 3' (the SEQ ID of which is given each combination of recognition arms and cleavage sites in the following table.

| SLS code | Recognition arm I | Recognition arm III | Cleavage Site | SEQ ID NO |
|---|---|---|---|---|
| 107 | CGCG | AAUU | A/U | SEQ ID NO: 13 |
| 108 | CUAG | AAUU | A/U | SEQ ID NO: 14 |
| 113 | UAUA | AAUU | A/U | SEQ ID NO: 15 |
| 115 | UGCA | AAUU | A/U | SEQ ID NO: 16 |
| 208 | CUAG | ACGU | A/U | SEQ ID NO: 17 |
| 213 | UAUA | ACGU | U | SEQ ID NO: 18 |
| 215 | UGCA | ACGU | A/U | SEQ ID NO: 19 |
| 313 | UAUA | AGCU | A/U | SEQ ID NO: 20 |

2. Preparation of RNA

Preparation of RNA was conducted as described in Example 1 above.

3. Spontaneous Cleavage Reaction:

Reactions (10 µl) were normally carried out in the presence of 5 pmol precursor ribozyme (SLS-transcripts), 50 mM Tris-Cl (pH-7.5), 1 mM EDTA (pH-7.5), 0.05% SDS and 300 mM $MgCl_2$. The reactions were preincubated at 95° C. for 1 min in order to eliminate alternative RNA conformations which may have formed furing storage at −20° C. The reactions were incubated at 37° C. for 1 hour or overnight and stopped by adding a dye solution containing 10 M urea and 10 mM EDTA and put on ice. The samples were denatured at 80° C. for 5 min and run on 15% polyacrylamide 7 M urea gel.

(b) Results

Figure 11B:
FIG. 11 shows the cleavage results of a catalytic system comprising the closed-circle composite molecule of FIG. 2(b)

The results of the polyacrylamide gel are shown in FIG. 11. A panel of 8 different circular ribozymes was examined for cascade activity. The cascade was initiated, by spontaneous cleavage as described above. As shown in FIG. 1, one of the ribozymes (#313) demonstrated a functioning catalytic cascade resulting in amplification in a positive feedback manner.

Example III
Ribozyme Inhibition by Blood and Various Materials Used for DNA Preparation All amplification techniques require a sample preparation step to release nucleic acids and eliminate inhibition of the reactions by blood components. Several materials like SDS, phenol and guanidinium are used in these preparations. An amplification reaction without the need of a sample prep step is to be performed. Ribozyme activity in the presence of blood, with and without nucleic acid releasing agents, was tested. Both RNA-only and modified ribozymes were examined.

(a) Method

1. Oligonucleotides:

Oligodeoxyribonucleotides were purchased from the unit for molecular biology of the Haddassa Hospital, Mount Scopus, Jerusalem. The modified ribozyme was synthesized by RPI, Boulder, Co. The Ampliscribe T7 transcription kit (Epicenter Technologies) was used for all RNA synthesis. [$\gamma^{32}$P] ATP [6000 ci/mmol] and [$\alpha^{32}$P] UTP [3000 Ci/mmol] were purchased from Rotem Industries Ltd., Israel. T4 Polynucleotide kinase was purchased from NEB, Beverly, Mass.

2. Ribozymes:

DS-LS-RzA3-6: 5' <u>GCAACAGTGGAGGAAAGCC</u>UACgucUGGUACGUCCA (SEQ ID NO: 3)

cugaugagGCCGAAAGGCcgaaacGUAGUAAA 3'

Lowercase—ribonucleotides;
Uppercase—2'-O-Methyl modification;
Underlined uppercase—deoxyribonucleotides.

HH8 (RNA transcript): 5' GGCGACCCUGAUGAGGC-CGAAAGGCCGAAACAUUAA 3' (SEQ ID NO:21).

3. Labeling of Modified Ribozyme:

50 pmoles of the ribozyme, 10 units of T4 Polynucleotide kinase and 20 µCi[$\gamma^{32}$P] ATP were incubated in 1x reaction buffer in a total volume of 10 µl at 25° C. for 1 hr. The reaction was terminated by incubation at 60° C. for 10 minutes.

4. Preparation of RNA:

HH8 template DNA oligonucleotide was purified by electrophoresis on 15% polyacrylamide 7 M urea gel, UV-shadowed and eluted overnight at room temperature in 0.5 M Tris-Cl (pH-7.5), 0.1% SDS and 0.1 mM EDTA. Eluted DNA was precipitated with 0.1 volume of 3 M sodium acetate and 3 volumes of ethanol, resuspended in 0.1 XTE (1 mM Tris-Cl pH-7.0 and 0.1 mM EDTA) and stored at −20° C. until use. Purified oligonucleotide was annealed to complementary non-template T7 RNA polymerase promoter oligonucleotide (TAATACGACTCACTATAGG(SEQ ID NO:12)) in 20 µM each by incubating at 95° C. for 15 seconds and at 70° C., 60° C., 55° C., 50° C., 45° C., 40° C. and 37° C. for 5 min at each temperature. Transcription reaction mixture (50 µl) contained 2 µM of annealed DNA, 1x reaction buffer, 10 mM Dithiothreitol, 2 mM ATP, CTP and GTP, 1 mM UTP, 25 mCi [$a^{32}$ P] UTP and 1.1 mM $MgCl_2$. The mixture was incubated for 1 hr at 37° C. and then for 5 minutes at 80° C. to deactivate the enzyme. The RNA was precipitated as described. Transcripts were purified by electrophoresis on 15% polyacrylamide 7 M urea gel. RNA was located by autoradiography and eluted as described. Eluted RNA was precipitated as described, resuspended in 0.1x TE and counted in scintillation flour (Luma LSC).

5. Cleavage reaction:

Reactions (10 μl) were normally carried out in the presence of 0.5 pmol modified ribozyme or HH8, 50 mM Tris-Cl (pH-7.5), 1 mD EDTA (pH-7.5), 0.05% SDS and 30 mM MgCl₂. 1 μl of whole blood or 0.2 μl of whole blood and the additional component were added (See FIG. 1). The reactions were incubated at 37° C. for 1 hour and stopped by adding a dye solution containing 10 M urea and 10 mM EDTA and put on ice. The samples were denatured at 80° C. for 5 min and run on 15% polyacrylamide 7 M urea gel.

(b) Results

Figure 12B:
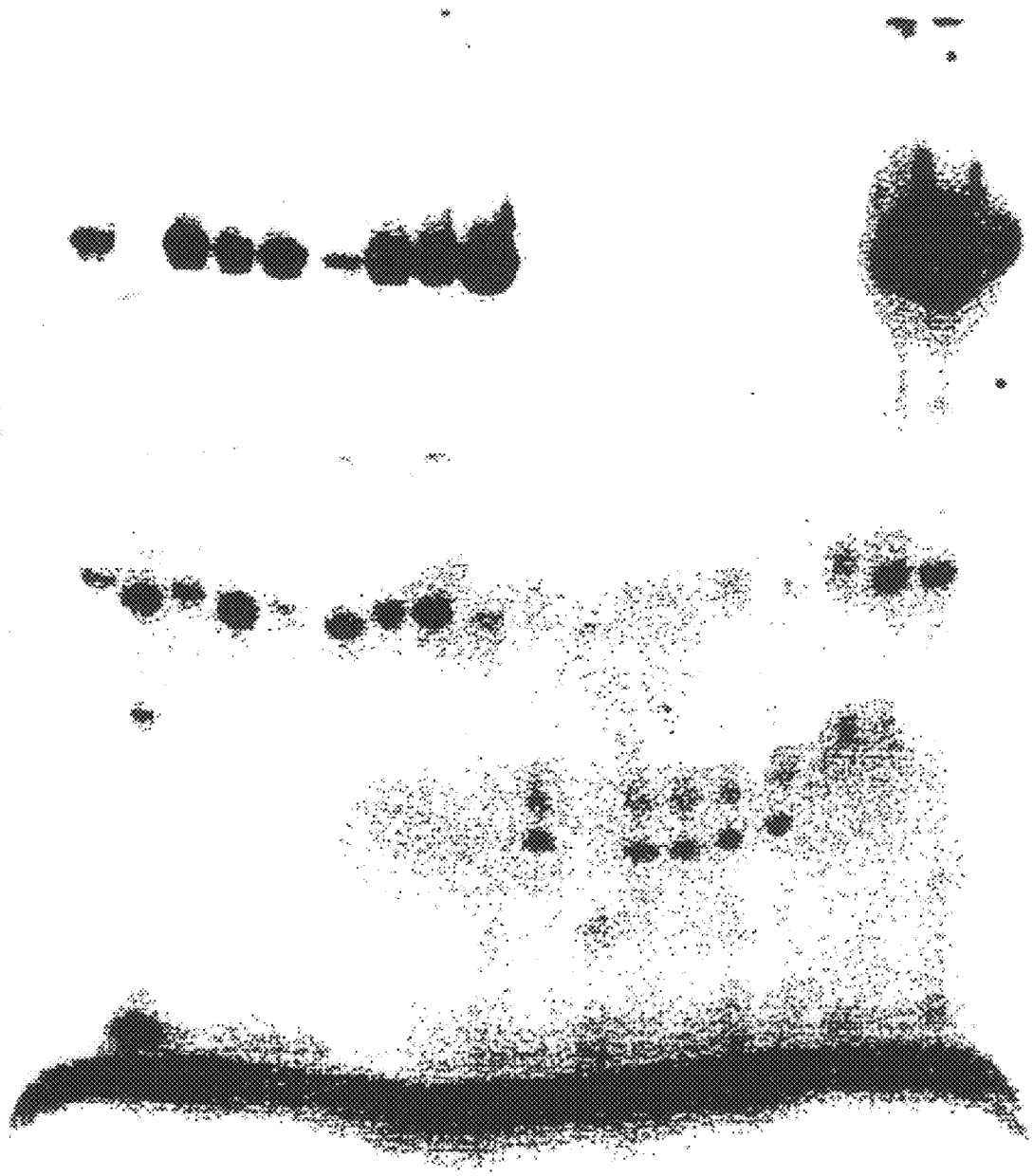
FIG. 12 shows the cleavage results of ribozyme in the presence of untreated blood and denaturing agents.

The results are shown in FIG. 12, wherein 0.5 pmol or ribozymes were present in each sample and 1 μl blood was mixed with either 10% SDS 4 M guanidine isocyanate or phenol chloroform 1:1, 1 μl of each treated blood sample or the agent alone was added to the reaction test. The results of ribozyme activity is not inhibited by either 1% SDS, 0.35 M guanidine or by 5% phenolOchloroform whether blood is present or not. Untreated blood degrades the RNA part of the ribozymes. These results show one of the advantages of the ribozyme based detection method of the invention in that denaturing agents used in the preparation of the catalytic sample do not hinder catalytic activity of the ribozyme.

We claim:

1. A method for detecting the presence of a catalytically active initiation ribozyme in a medium, comprising the steps of:
   (a) providing a catalytic system comprising catalytic system ribozymes which are catalytically inactive or spatially confined such that they cannot exert their catalytic activity on their target, the target of the catalytic system ribozymes being other catalytic system ribozymes,
   wherein the catalytic activity of the catalytic system ribozymes on said other catalytic system ribozymes cause either:
   (i) activation of inactive catalytic system ribozymes, or
   (ii) release of spatially confined catalytic system ribozymes to allow them to reach their targets,
   wherein at least some of the catalytic system ribozymes are a target of the catalytic activity of the initiation ribozyme, the catalytic activity of the initiation ribozyme on said some of the catalytic system ribozymes being that of (i) or (ii) above, and
   wherein the catalytic activity of the catalytic system ribozymes causes a change in the detectable properties of a detectable label;
   (b) contacting the medium with said catalytic system;
   (c) providing conditions permitting said catalytically active initiation ribozyme and catalytically active catalytic system ribozymes to exert their catalytic activity, whereby the presence of a catalytically active initiation ribozyme gives rise to a reaction cascade in which catalytic system ribozymes are activated or freed into the medium; and
   (d) detecting said detectable properties, a change in said properties being an indication of the presence of an active initiation ribozyme in said medium.

2. A method of detecting the presence of an assayed biomolecule in a test sample comprising the steps of:

(a) contacting the sample with a detection system under conditions which enable production of a catalytically active initiation ribozyme only if the assayed biomolecules are present in the sample; and (b) detecting the presence of the catalytically active initiation ribozyme according to the method of claim 1, the presence thereof indicating the presence of the assayed biomolecule in the sample.

3. A method of detecting the presence of assayed biomolecules in a test sample, comprising the steps of:

(a) providing a first complex molecule comprising an initiation ribozyme under conditions wherein the ribozyme is catalytically inactive, and a recognition biomolecule capable of specifically recognizing and binding said assayed biomolecule;

(b) contacting said first complex molecule with the test sample under conditions which allow binding between said recognition biomolecule and said assayed biomolecule while maintaining the conditions which render the ribozyme catalytically inactive;

(c) removing unbound first complex molecules;

(d) providing different conditions wherein the initiation ribozyme is rendered active; and (e) detecting the presence of the catalytically active initiation ribozyme according to the method of claim 1, the presence thereof indicating the presence of the assayed biomolecule in the sample.

4. The method according to claim 3, wherein the conditions in (a) are essentially lack of magnesium ions and step (d) comprises adding to the reaction medium magnesium ions in a concentration sufficient to render said initiation ribozyme catalytically active.

5. A method of detecting the presence of assayed biomolecules in a test sample, comprising the steps of:

(a) providing a first complex molecule comprising an initiation ribozyme under conditions wherein the ribozyme is catalytically inactive, and a recognition biomolecule capable of specifically recognizing and binding said assayed biomolecule, said ribozyme being linked to a cleavable nucleic acid sequence capable of being cleaved by a catalytically activated initiation ribozyme, wherein cleavage of said cleavable sequence releases catalytically active initiation ribozyme to the surrounding medium;

(b) contacting said first complex molecule with the test sample under conditions which allow binding between said recognition biomolecule and said assayed biomolecule while maintaining the conditions which render the ribozyme catalytically inactive;

(c) removing unbound first complex molecules;

(d) providing different conditions wherein the initiation ribozyme is rendered catalytically active to cause cleavage of said cleavable sequence and thus release the initiation ribozyme into the surrounding medium; and (e) detecting the presence of the catalytically active initiation ribozyme according to the method of claim 1, the presence thereof indicating the presence of the assayed biomolecule in the sample.

6. A method of detecting the presence of assayed biomolecules in a test sample, comprising the steps of:

(a) providing a hybrid molecule comprising an initiation ribozyme linked to a cleavable nucleic acid sequence which is capable, when single stranded, of being cleaved by the initiation ribozyme, cleavage of said cleavable sequence releasing catalytically active initiation ribozyme to the surrounding medium, the hybrid molecule further comprising a recognition biomolecule capable of specifically recognizing and binding said assayed biomolecule, said cleavable sequence and a part of said recognition biomolecule being double stranded;

(b) contacting said hybrid molecule with the test sample under conditions which allow displacement of one strand of the double stranded part of the recognition biomolecule and the cleavable nucleic acid sequence by an essentially perfectly matched assayed biomolecule;

(c) providing conditions allowing for cleavage by catalytically active ribozymes to cause cleavage of the single stranded cleavable sequence, thereby releasing catalytically active initiation ribozyme into the surrounding medium; and (d) detecting the presence of the catalytically active initiation ribozyme according to the method of claim 1, the presence thereof indicating the presence of the assayed biomolecule in the sample.

7. A method of detecting the presence of assayed biomolecules in a test sample, comprising the steps of:

(a) providing a second complex molecule comprising an initiation ribozyme and a recognition biomolecule capable of specifically recognizing and binding said assayed biomolecules, said ribozyme linked to a cleavable nucleic acid sequence capable of being cleaved by catalytically active initiation ribozyme, cleavage of said cleavable sequence releasing catalytically active initiation ribozyme to the surrounding medium, said second complex molecule also comprising an inhibitory moiety capable of inhibiting the catalytic activity of said initiation ribozyme;

(b) contacting said second complex molecule with the test sample under conditions which allow binding between said recognition molecules and said assayed biomolecule while maintaining the inhibitory moiety in its inhibiting form;

(c) removing unbound second complex molecules;

(d) modifying said inhibitory moiety in the bound second complex molecules so as to remove its inhibitory effect thereby causing cleavage of said cleavable sequence and releasing the initiation ribozyme into the surrounding medium; and (e) detecting the presence of the catalytically active initiation ribozyme according to the method of claim 1, the presence thereof indicating the presence of the assayed biomolecule in the sample.

8. The method according to claim 1, wherein the catalytic system comprises:

a first and a second ribozyme, both being catalytically inactive, said first ribozyme becoming catalytically active when subjected to the catalytic activity of said second ribozyme and said second ribozyme becoming catalytically active when subjected to the catalytic activity of said first ribozyme, at least one of said first or said second ribozyme becoming catalytically active also when subjected to the catalytic activity of said initiation ribozyme, at least one of said first or said second ribozyme comprising a label such that when subjected to the catalytic activity of the other ribozyme there is a change in the detectable properties of said label; and wherein, in step (c), conditions are provided in which said initiation ribozyme and said first and said second ribozyme can exert their catalytic activity.

9. The method according to claim 1, wherein the catalytic system comprises:
a first composite nucleic acid molecule, comprising a first ribozyme of a kind capable of cleaving a first cleavable nucleic acid sequence, linked to a second cleavable nucleic acid sequence, wherein cleavage of said second cleavable nucleic acid sequence releases said first ribozyme from said first composite nucleic acid molecule, and
a second composite nucleic acid molecule, comprising a second ribozyme of a kind capable of cleaving said second cleavable nucleic acid sequence linked to said first cleavable nucleic acid sequence, wherein cleavage of said first cleavable nucleic acid sequence releases said second ribozyme from said second composite molecule,
at least one of said first or second cleavable nucleic acid sequences being cleavable also by said initiation ribozyme,
said first composite and said second composite nucleic acid molecules being separated from one another to avoid contact between the two composite molecules,
at least one of said first and said second composite molecules comprising a detectable label, said label being released to the reaction medium following cleavage by the ribozyme comprised in the other composite molecule;
wherein, in step (c), conditions are provided which enable ribozyme cleavage of the first and second cleavable nucleic acid sequence and which allow migration of cleaved ribozymes between said first and said second composite nucleic acid molecules; and
wherein, in step (d), released label is detected, the presence of released label in the medium indicating the presence of the catalytically active initiation ribozyme in the medium.

10. The method according to claim 9, wherein the first and second composite nucleic acid molecules are located on opposite sides of a porous membrane blocking their passage therethrough while enabling passage of first and second free ribozymes.

11. The method according to claim 9, wherein the first and second composite nucleic acid molecules are immobilized on a substrate.

12. The method according to claim 11, wherein the substrate is a bead.

13. The method according to claim 9, wherein the first and second composite nucleic acid molecules are linked to moieties having the same electrical charges.

14. The method according to claim 1, wherein the catalytic system comprises:
a third ribozyme, which is an inactive catalytic system ribozyme, that becomes active when subjected to the catalytic activity of other molecules of catalytically active third ribozymes which are catalytic system ribozymes,
said inactive third ribozyme becoming active also when subjected to the catalytic activity of said initiation ribozyme,
said third ribozyme comprising a label such that when subjected to the catalytic activity of the other third ribozyme there is a change in the detectable properties of said label; and
wherein, in step (c), conditions are provided suitable for said third ribozyme and said initiation ribozyme to exert their catalytic activity.

15. The method according to claim 14, wherein the catalytic system comprises:
a composite nucleic acid molecule comprising a ribozyme which has a cleavable nucleic acid sequence, said composite molecule being in the form of a closed circle and said cleavable nucleic acid sequence being cleavable by the composite molecule in an open form,
said cleavable nucleic acid sequence being cleavable also by the initiation ribozyme, and
said composite nucleic acid molecule carrying a detectable label which changes its detectable properties upon opening of the closed composite molecule; and
wherein, in step (c), conditions are provided which enable ribozyme cleavage of said composite nucleic acid molecule and migration of said composite nucleic acid molecule.

16. The method according to claim 14, wherein the catalytic system comprises:
a sixth ribozyme which is a catalytic system ribozyme having, in a region thereof essential for its catalytic activity, an extra nucleic acid sequence, wherein said nucleic acid sequence renders the catalytic system ribozyme inactive,
wherein splicing of said extra nucleic acid sequence renders the sixth ribozyme active,
and wherein said extra nucleic acid sequence is capable of being spliced from the inactive catalytic ribozyme by the sixth ribozyme, said sixth ribozyme comprising a detectable label which changes its detectable properties upon splicing of the extra nucleic acid sequence; and
wherein, in step (c), conditions are provided which allow ribozyme splicing.

17. The method according to claim 1, wherein the catalytic system comprises
a composite nucleic acid molecule, comprising a labelled ribozyme linked to a cleavable nucleic acid sequence in an orientation or at a location which prevents cleavage of said cleavable nucleic acid sequence by said ribozyme while present in the composite molecule, said cleavable nucleic acid sequence being cleavable by said ribozyme when said ribozyme is present in a free form, thereby releasing said labelled ribozyme from said composite molecule,
said cleavable nucleic acid sequence being cleavable also by said initiation ribozyme, and
said composite nucleic acid molecules being separated from one another to avoid contact therein between;
wherein, in step (c), conditions are provided which enable cleavage by said labelled ribozyme and said initiation ribozyme and which allow migration of cleaved ribozymes between the separated composite nucleic acid molecules; and
wherein, in step (d), released label is detected, the presence of released label in the medium indicating the presence of the catalytically active ribozyme in the medium.

18. The method according to claim 17, wherein each composite molecule is immobilized on a substrate.

19. The method according to claim 17, wherein each composite molecule is linked to a charged moiety, all moieties in the reaction mixture having the same charge.

20. A method of detecting an assayed biomolecule in a test sample, wherein the assayed biomolecule is a nucleic acid sequence and the method comprises the steps of:
(a) incubating the test sample with a detection system comprising:
a third composite molecule comprising a third single-stranded oligonucleotide sequence that is complementary to the 5'-part of the assayed nucleic acid sequence, wherein said third single-stranded oligonucleotide sequence is linked to a part of the initiation ribozyme; and a fourth composite molecule comprising a fourth single-stranded oligonucleotide sequence that is complementary to the remaining 3'-part of the assayed nucleic acid sequence, wherein said fourth single-stranded oligonucleotide sequence is linked to a part of the initiation ribozyme required to complete the ribozyme linked to said third single-stranded oligonucleotide sequence to give a complete initiation ribozyme;

(b) providing conditions allowing hybridization of said third and fourth single-stranded oligonucleotide sequences with the assayed nucleic acid sequence and which enable assembly of a full initiation ribozyme from its parts; and (c) detecting the presence of the catalytically active initiation ribozyme according to the method of claim 1, the presence thereof indicating the presence of the assayed biomolecule in the sample.

21. A method of detecting an assayed biomolecule in a test sample, wherein the assayed biomolecule is a nucleic acid sequence and the method comprises the steps of:

(a) incubating the test sample with a detection system comprising:

a ribozyme of the hammerhead type wherein some of the double-stranded portion of Stem-II has been shortened and wherein the remaining double-stranded Stem-II is attached to two single-stranded sequences, one being complementary to the 3'-end of the assayed nucleic acid sequence and the other being complementary to the 5'-end of the nucleic acid sequence, wherein said ribozyme is inactive and hybridization of said two single-stranded sequences to complementary sequences renders the ribozyme catalytically active;

(b) providing conditions allowing hybridization of said ribozyme with said assayed nucleic acid sequence; and (c) detecting the presence of the catalytically active initiation ribozyme according to the method of claim 1, the presence thereof indicating the presence of the assayed biomolecule in the sample.

22. The method according to claim 1, for detecting the presence in the medium of a catalytically active initiation ribozyme having the activity of cleavage, wherein the catalytic system comprises:

a fourth ribozyme of a kind capable of ligating parts of a fifth ribozyme, linked to a nucleic acid sequence cleavable by the initiation ribozyme, cleavage of said nucleic acid sequence releasing catalytically active fourth ribozyme to the surrounding medium, two parts of a fifth ribozyme which are capable of being ligated by the fourth ribozyme to give a catalytically active fifth ribozyme, said fifth ribozyme being of a kind capable of ligating parts of a fourth ribozyme, and two parts of a fourth ribozyme which are capable of being ligated by the fifth ribozyme to give catalytically active fourth ribozyme, said fourth ribozyme being separate from the two parts of the fifth ribozyme to avoid contact therebetween, wherein at least one of said fourth or said fifth ribozyme carries labels which changes its detectable properties upon ligation;

wherein step (c) comprises providing conditions which enable ribozyme cleavage and which allow migration of a cleaved full fourth ribozyme to the two parts of the fifth ribozyme and providing or maintaining conditions allowing ribozyme ligation.

23. The method according to claim 1, for detecting the presence in the medium of catalytically active initiation ribozyme having the activity of ligation, wherein the catalytic system comprises:

two parts of a fifth ribozyme which are capable of being ligated by a fourth ribozyme to produce a catalytically active fifth ribozyme, said fifth ribozyme being of a kind capable of ligating parts of a fourth ribozyme, and two parts of a fourth ribozyme which are capable of being ligated by a fifth ribozyme to produce a catalytically active fourth ribozyme, said fourth ribozyme being of a kind capable of ligating parts of the fifth ribozyme, wherein either said two parts of the fifth ribozyme or said two parts of the fourth ribozyme are capable of being ligated by a catalytically active initiation ribozyme, and at least one of said fourth or said fifth ribozyme carries labels which changes its detectable properties upon ligation; and wherein step (c) comprises providing conditions allowing ribozyme ligation.

24. A kit for detecting the presence of a catalytically active initiation ribozyme in a medium comprising:

a catalytic system comprising (a) assay ribozymes which are catalytically inactive or spatially confined such that they cannot exert their catalytic activity on their target, the target of the assay ribozymes being other ribozymes of the catalytic system, their catalytic activity on such other ribozymes causing either:

(i) activation of inactive assay ribozymes, or (ii) release of spatially confined assay ribozymes to allow them to reach their targets, at least some of the assay ribozymes of the catalytic system being a target of the catalytic activity of the initiation ribozyme, the catalytic activity of the initiation ribozyme on said some of the assay ribozymes being that of (i) or (ii) above; and (b) a detectable label having detectable properties, wherein the catalytic activity of the assay ribozymes cause a change in the detectable properties.

25. The kit according to claim 24, wherein the catalytic system comprises:

assay ribozymes which are first and second ribozymes, both being catalytically inactive, wherein said first ribozyme is capable of becoming catalytically active when subjected to the catalytic activity of said second ribozyme and said second ribozyme is capable of becoming catalytically active when subjected to the catalytic activity of said first ribozyme, at least one of said first or second ribozymes also being capable of becoming catalytically active when subjected to the catalytic activity of said initiation ribozyme, and at least one of said first or said second ribozyme carrying a label such that upon catalytic activity of the other of said first or said second ribozyme there is a change in the detectable properties of said label.

26. The kit according to claim 24, wherein the catalytic system comprises:

a first composite nucleic acid molecule, comprising an assay ribozyme which is a first ribozyme of a kind capable of cleaving a first cleavable nucleic acid sequence, linked to a second cleavable nucleic acid sequence, wherein cleavage of said second cleavable nucleic acid sequence releases said first ribozyme from said first composite nucleic acid molecule, and a second composite nucleic acid molecule, comprising an assay ribozyme which is a second ribozyme of a kind capable of cleaving said second cleavable nucleic acid sequence, linked to a first cleavable nucleic acid sequence, wherein cleavage of said first cleavable nucleic acid sequence releases said second ribozyme from said second composite molecule, wherein at least one of said first or second cleavable nucleic acid sequences is cleavable also by said initiation ribozyme, said first composite and second composite nucleic acid molecules are separated from one another to avoid contact between the two composite molecules, and at least one of said first and said second composite molecules carries a detectable label, said label being released to the reaction medium following cleavage by the ribozyme comprised in the other composite molecule.

27. The kit according to claim 24, wherein the catalytic system further comprises:

an assay ribozyme which is a catalytically inactive third ribozyme, wherein each molecule of catalytically inactive third ribozyme is capable of becoming catalytically active when subjected to the catalytic activity of other molecules of catalytically active third ribozyme, said catalytically inactive third ribozyme is also capable of becoming active when subjected to the catalytic activity of said initiation ribozyme, and said third ribozyme carries a label such that when subjected to the catalytic activity of a catalytically active third ribozyme, there is a change in the detectable properties of said label.

28. The kit according to claim 24, wherein the catalytic system comprises:

a composite nucleic acid molecule, comprising a labelled assay ribozyme linked to a cleavable nucleic acid sequence in an orientation or at a location which prevents cleavage of said nucleic acid sequence by said assay ribozyme while present in the composite molecule, said nucleic acid sequence being cleavable by said assay ribozyme when it is present in a free form, thereby releasing said labelled assay ribozyme from said composite molecule, said cleavable nucleic acid sequence being cleavable also by said initiation ribozyme, said composite molecules being separated from one another to avoid contact therebetween.

29. A method of detecting an assayed biomolecule in a test sample, wherein the assayed biomolecule is a nucleic acid sequence and the method comprises the steps of:

(a) contacting the sample with a detection system comprising:

a first oligonucleotide molecule having a double-stranded promoter, a single-stranded oligonucleotide sequence that is an initiation ribozyme, a single-stranded sequence that is a cleavable sequence capable of being cleaved by a catalytically active initiation ribozyme, and a single-stranded sequence which is complementary to the 5'-part of the assayed nucleic acid sequence; and a second oligonucleotide molecule having a single-stranded sequence that is complementary to the 3'-part of the assayed nucleic acid sequence and further comprises a single-stranded triggering oligonucleotide template which can be transcribed to give a triggering oligonucleotide sequence, said triggering oligonucleotide sequence capable, in the presence of a back promoter construct and DNA polymerase, to trigger a reaction in a transcription system wherein the sequence to which it is attached is transcribed;

(b) providing conditions which allow the hybridization of said first and said second oligonucleotide molecule to the assayed nucleic acid sequence;

(c) adding a transcription system, under conditions which allow transcription, whereby triggering oligonucleotide sequence is transcribed, said triggering oligonucleotide sequence, in the presence of a back promoter, DNA polymerase and transcription system and under conditions allowing hybridization, DNA polymerization and transcription, results in the transcription of a final oligonucleotide transcript comprising an initiation ribozyme linked to a cleavable sequence capable of being cleaved by catalytically active initiation ribozyme;

(d) providing conditions which allow cleavage of said cleavable sequence by said catalytically active ribozyme, to cause cleavage of said cleavable sequence and thus release thereof into the surrounding medium; and (e) detecting the presence of the catalytically active initiation ribozyme according to the method of claim 1, the presence thereof indicating the presence of the assayed biomolecule in the sample.

* * * * *